US005532243A

United States Patent [19]

Gilligan

[11] Patent Number: 5,532,243
[45] Date of Patent: Jul. 2, 1996

[54] ANTIPSYCHOTIC NITROGEN-CONTAINING BICYCLIC COMPOUNDS

[75] Inventor: Paul J. Gilligan, Claymont, Del.

[73] Assignee: The DuPont Merck Pharmaceutical Company, Wilmington, Del.

[21] Appl. No.: 836,230

[22] Filed: Feb. 14, 1992

[51] Int. Cl.[6] .................. A61K 31/495; A61K 31/40; C07D 217/18; C07D 239/00
[52] U.S. Cl. .................. 514/255; 514/258; 514/259; 514/307; 514/314; 514/339; 514/412; 514/414; 514/415; 514/419; 544/242; 544/278; 544/282; 544/296; 544/333; 544/335; 544/336; 544/405; 546/143; 546/144; 546/145; 546/146; 546/147; 546/148; 546/149; 546/174; 546/176; 546/14; 546/276.7; 546/277.1; 546/122; 544/237; 544/284; 544/285; 544/283
[58] Field of Search .................. 546/153, 149, 546/143, 144, 145, 146, 147, 148, 174, 176, 272, 273, 455, 456, 465, 512, 513; 514/412, 414, 415, 419, 255, 258, 259, 307, 314, 339; 544/242, 278, 282, 296, 333, 335, 336, 405

[56] References Cited

U.S. PATENT DOCUMENTS

| 2,387,751 | 10/1945 | Dickey et al. | 546/153 |
| 3,127,413 | 3/1964 | Gray et al. | 540/521 |
| 3,689,492 | 9/1972 | Schroeder et al. | 540/521 |
| 4,954,509 | 9/1990 | Vecchietti et al. | 514/304 |
| 5,075,303 | 12/1991 | Cliffe et al. | 546/153 |
| 5,175,157 | 12/1992 | Psiorz et al. | 514/213 |
| 5,216,018 | 6/1993 | Ciganek | 514/416 |

FOREIGN PATENT DOCUMENTS

| 0196132 | 1/1986 | European Pat. Off. . |
| 3721723 | 12/1989 | Germany . |
| 937218 | 9/1963 | United Kingdom . |
| 1141664 | 1/1969 | United Kingdom . |

OTHER PUBLICATIONS

Achini et al., Helv. Chim. Acta. 1974, 57:572.
Janssen et al., J. Med. Pharm. Chem. 1959, 1:281.
Gray et al., J. Am. Chem. Soc. 1962, 84:89.

Primary Examiner—C. Warren Ivy
Assistant Examiner—Raymond Covington
Attorney, Agent, or Firm—Karen H. Kondrad; Gerald J. Boudreaux

[57] ABSTRACT

There are provided nitrogen-containing bicyclic compounds, pharmaceutical compositions containing these compounds and methods of using these compounds to treat physiological or drug-induced psychosis or diskinesia in a mammal.

48 Claims, No Drawings

ANTIPSYCHOTIC NITROGEN-CONTAINING BICYCLIC COMPOUNDS

FIELD OF THE INVENTION

This invention relates to novel nitrogen-containing bicyclic compounds, pharmaceutical compositions containing these compounds and methods of using these compounds to treat physiological or drug induced psychosis and as antidyskinetic agents.

BACKGROUND OF THE INVENTION

U.S. Pat. No. 3,127,413 (Gray) discloses octahydroisoindoles of the formula:

Ar—Alk—N[structure with OR and OR' groups]

wherein:
  Ar represents a radical from an aromatic ring system which is monocyclic or bicyclic;
  Alk represents on alkylene chain, straight or branched, containing at least one and not more than three carbon atoms;
  R is H or acyl; and
  R' is lower-alkyl.

The octahydroisoindoles are useful as tranquilizing agents and for potentiating the action of barbiturates.

Processes for preparing trisubstituted perhydro isoindolines of the following formula are described by Achini et al, Helvetica Chimica Acta, 57, Fasc. 3, pp. 572–585 (1974):

[structure with $R^2$, $R^3$, H, and N—$R^1$ groups]

wherein:
  $R^1$ is H or $COC_6H_5$;
  $R^2$ is $NR^4R^5$ Br, OH, phenyl, or CN;
  $R^3$ is H or OH; and
  $R^4$, $R^5$ are H or lower alkyl.

German Patent 3721723 (Hoechst AG) describes substituted 6-Oxo-Decahydroisoquinolines of the formula:

[structure with N—$R^1$, $R^2$, and O groups]

wherein:
  $R^1$ is benzyl, $C_1$–$C_4$ alkoxycarbonyl or 2,2,2-Trichloro-ethoxycarbonyl; and
  $R^2$ is $C_1$–$C_8$ alkyl, $C_2$–$C_8$ alkenyl, cyclohexyl-$C_1$–$C_4$ alkyl, 9-fluorenyl, 1-Cyano-1-phenylmethyl or phenyl-$C_1$–$C_4$ alkyl.

These compounds are useful as tranquilizing agents.

U.S. Pat. No. 3,689,492 (Schroeder et al.) discloses a compound having the formula:

[structure with HO-phenyl, piperidine, $CH_2—(CH_2)_2—C(=O)$-phenyl-F groups]

This compound is useful as an analgesic in warm-blooded animals.

U. K. Patent No. 1,141,664 (Jansen) discloses piperidine compounds having the formula:

$$Y—CO—CH_2—CH_2—CH_2—N\text{[ring with OH and Z]}$$

wherein Y is Ar or $Ar^3$ and Z is $Ar^1$ or $Ar^2$, Ar being phenyl, halophenyl or lower alkoxy phenyl, $Ar^1$ being dihalophenyl, trihalophenyl, lower alkyl - halo- phenyl or trifluoromethy - halo - phenyl, $Ar^2$ being halophenyl and $Ar^3$ being di - halo - phenyl or lower alkyl - halo - phenyl, with the proviso that when Y is Ar then Z is $Ar^1$, and when Y is $Ar^2$ then Z is $Ar^2$. These compounds are useful as psychotropic and neuroleptic agents.

European Patent Application No. 0 196 132 (Kennis and Vandenberk) discloses compounds having the formula:

[structure with Q—Alk—N, R, X, $R^1$, $R^2$ groups]

wherein X is O or S and Q is a radical of formula

[structure with $R^3$, $R^4$, $Y^1$, $Y^2$, N, H groups]

or a radical of formula

[structure with A, Z, N, $R^5$, O groups]

These compounds are useful as antipsychotics.

Janssen et al., Journal of Med. and Pharm. Chem., vol. 1, 281–297 (1959), disclose compounds having the formula:

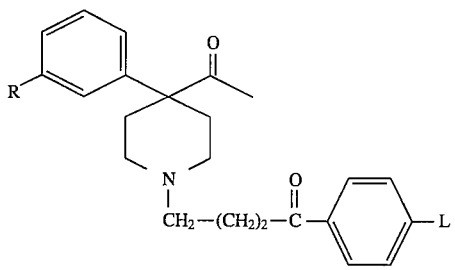

wherein L=H or F and R=H, F, Cl, or CH$_3$). The authors discuss the CNS depressant properties of these compounds.

Compounds of the present invention demonstrate sigma receptor affinity. It is this sigma receptor affinity of the compounds of the present invention which makes them so advantageous over the compounds in the prior art. Traditionally, antipsychotic agents have been potent dopamine receptor antagonists. For example, phenothiazines such as chlorpromazine and most butyrophenones such as haloperidol are potent dopamine receptor antagonists. These dopamine receptor antagonists are associated with a high incidence of side effects, particularly Parkinson-like motor effects or extra-pyramidal side-effects (EPS), and dyskinesias including tardive dyskinesias at high doses. Many of these side effects are not reversible even after the dopamine receptor antagonist agent is discontinued.

The present invention is related to antipsychotic agents which are sigma receptor antagonists, not traditional dopamine receptor blockers known in the art, and therefore the compounds of the present invention have low potential for the typical movement disorder side-effects associated with the traditional dopamine antagonist antipsychotic agents while they maintain the ability to antagonize aggressive behavior and antagonize hallucinogenic-induced behavior.

SUMMARY OF THE INVENTION

Compounds of this invention are novel antagonists of sigma receptors, which may be useful for the treatment of physiological and drug-induced psychosis and dyskinesia.

The compounds of the present invention are nitrogen-containing bicyclic compounds of the formula:

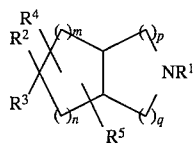
(I)

or a pharmaceutically acceptable salt or pro-drug thereof, wherein:

m is 1 or 2;

n is 1 or 2;

p is 1 or 2;

q is 1 or 2;

provided that m and n cannot both be 2 or p and q cannot both be 2;

$R^1$ may be H, alkyl of 1 to 6 carbons, cycloalkyl of 3 to 6 carbons, cycloalkyl-alkyl of 4 to 8 carbons, alkenyl of 3 to 6 carbons, phenyl-alkyl (1 to 6 carbons) where the phenyl group is optionally substituted by $R^6$ and $R^7$ and where the alkyl group is optionally substituted by oxo, hydroxyl groups or hydrogen, heteroaryl-alkyl (1 to 6 carbons) or naphthyl-alkyl (1 to 6 carbons) and where the alkyl group is optionally substituted by oxo, hydroxyl groups or hydrogen, $R^1$ may also be drawn from the following groups:

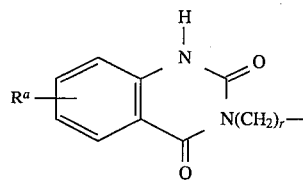

where:

r=1 or 2, $R^a$=H, alkyl of 1 to 6 carbons, halogen, alkoxy of 1 to 6 carbons or OH, and

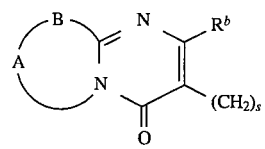

where:

s=1 or 2,

B=S, CH$_2$ or CH=CH,

A=(CH$_2$)$_2$, (CH$_2$)$_3$ or CH=CH, $R^b$=H or alkyl of 1 to 6 carbons;

$R^2$ may be H, OH, alkoxy of 1 to 6 carbons or O$_2$CR$^{2a}$ provided that when $R^2$ is not H then $R^3$=R$^{3a}$ and provided that when $R^2$ is H then $R^3$=OR$^{3a}$ or SR$^{3a}$;

$R^{2a}$ may be alkyl of 1 to 10 carbons or phenyl;

$R^{3a}$ may be alkyl of 1 to 6 carbons, phenyl optionally substituted by $R^6$ and $R^7$, phenyl-alkyl (1 to 6 carbons) where the phenyl group is optionally substituted by $R^6$ and $R^7$, cycloalkyl of 3 to 6 carbons, cycloalkyl-alkyl of 4 to 12 carbons, naphthyl, heteroaryl or heteroaryl-alkyl (1 to 6 carbons);

$R^4$ and $R^5$ may independently be H or alkyl of 1 to 6 carbons;

$R^6$ and $R^7$ independently are selected at each occurrence from the group consisting of H, alkyl of 1 to 6 carbons, alkenyl of 2 to 6 carbons, OH, alkoxy of 1 to 6 carbons, alkythio of 1 to 6 carbons, alkylsulfinyl of 1 of 6 carbons, alkylsulfonyl of 1 to 6 carbons, NH$_2$, alkylamino of 1 to 6 carbons, dialkylamino of 2 to 12 carbons, NO$_2$, alkanoylamino of 2 to 6 carbons, CN, CO$_2$H, carboalkoxy of 2 to 10 carbons, CONH$_2$ or CONR$^8$R$^9$; and $R^8$ and $R^9$ independently are H or alkyl of 1 to 6 carbons; or $R^8$ and $R^9$ taken together may be alkylene of 3 to 6 carbons.

The compounds herein described may have asymmetric centers. All chiral, diastereomeric and racemic forms are included in the present invention. Many geometric isomers of olefins, C=N double bonds, described herein, and all such stable isomers are contemplated in the present invention.

Combinations of substituents and/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl. "Alkenyl" is intended to include hydrocarbon chains of either a straight or branched configuration and one or more unsaturated carbon-carbon bonds which may occur in any stable point along the chain, such as ethenyl, propenyl and the like.

As used herein, "aryl" or "aromatic residue" is intended to mean phenyl or naphthyl.

As used herein, the term heteroaryl is intended to mean a stable 5- to 7- membered monocyclic or bicyclic or 7- to 10-membered bicyclic heterocyclic ring which is either saturated or unsaturated, and which consists of carbon atoms and from 1 to 3 heteroatoms selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl, pyrimidinyl, pyrazinyl, quinolinyl, isoquinolinyl, indolyl, quinazolinyl, phthalizinyl, furanyl, thienyl or napthyridinyl.

The term "substituted" as used herein, means that one or more hydrogen on the designated atom is replaced with a selection from the indicated group, provided that the designated atom's normal valency is not exceeded, and that the substitution results in a stable compound.

As used herein the term cycloalkyl-alkyl is intended to mean a group comprising a cycloalkyl moiety as defined above and an alkyl moiety as defined above. The cycloalkyl-alkyl group may be attached to its pendant group at any carbon atom which results in a stable structure.

As used herein the term phenyl-alkyl is intended to mean a group comprising a phenyl moiety and an alkyl moiety as defined above. The phenyl-alkyl group may be attached to its pendant group at any carbon atom which results in a stable structure.

As used herein the term heteroaryl-alkyl is intended to mean a group consisting of a heteroaryl moiety as defined above and an alkyl moiety as defined above. The heteroaryl-alkyl group may be attached to its pendant group at any carbon atom which results in a stable structure.

By "stable compound" or "stable structure" is meant herein a compound that is sufficiently robust to survive isolation to a useful degree of purity from a reaction mixture, and formulation into an efficacious therapeutic agent.

As used herein, "pharmaceutically acceptable salts and prodrugs" refer to derivatives of the As used herein, "pharmaceutically acceptable salts and prodrugs" refer to derivatives of the disclosed compounds that are modified by making acid or base salts, or by modifying functional groups present in the compounds in such a way that the modifications are cleaved, either in routine manipulation or in vivo, to the parent compounds. Examples include, but are not limited to, mineral or organic acid salts of basic residues such as amines; alkali or organic salts of acidic residues such as carboxylic acids; acetate, formate and benzoate derivatives of alcohols and amines; and the like.

PREFERRED EMBODIMENTS

Preferred compounds in the present invention are those compounds of Formula (I) wherein:

$R^2$ is OH, and $R^2$=H when $R^3$=$OR^{3a}$

Specifically preferred compounds of the present invention are:

a) Cis-2-(4'-fluorophenethyl)-6-(4''-fluorophenyl)- 6-hydroxydecahydroisoquinoline.

b) Cis-2-(4'-pyridylmethyl)-6-(4''-fluorophenyl)-6-hydroxy decahydroisoquinoline.

c) Cis-2-(4'-pyridylmethyl)-6-(4''-fluorophenyl)-6-hydroxydecahydroisoquinoline, dihydrochloride salt.

d) Trans-2-Benzyl-6-(4'fluorophenyl)-6-hydroxy decahydroisoquinoline.

e) Trans-2-Benzyl-6-(4'-fluorophenyl)-6-hydroxy decahydroisoquinoline, major hydroxy epimer.

f) Trans-2-Benzyl-4-(4'-Fluorobenzyloxy)-decahydroisoquinoline.

g) Trans-2-Benzyl-4-(4'-fluorophenoxy)-decahydroisoquinoline.

Also provided in the present invention are pharmaceutical compositions comprising an effective amount of a compound of Formula (I) and a pharmaceutically acceptable carrier.

Further provided are methods of using the compounds of Formula (I) for the treatment of physiological or drug induced psychosis in a mammal as well as for the treatment of dyskinesia in a mammal.

DETAILED DESCRIPTION OF THE INVENTION

Compounds of Formula (I) may be prepared according to Scheme I. A compound of Formula (II) is treated with an organometallic reagent, $R^3M$, in an inert solvent to afford a compound of Formula (III) (Formula (I) where $R^2$=OH). The organometallic reagent, $R^3M$, may be prepared from a halide, $R^3X$ (where X=Cl, Br or I, preferably Br) and a metallating agent, such as alkali metals (e.g. lithium), alkaline earth metals (e.g. magnesium) or alkyl lithiums (e.g. n-butyl lithium or t-butyl lithium). Metallating agents include combinations of one of the above.

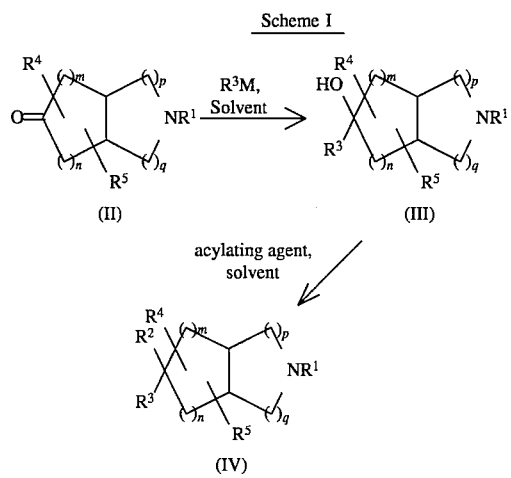

Scheme I reagents and an inorganic salt such as alkaline earth metal halides or transition metal halides, preferably CuBr, $ZnCl_2$ or $CeCl_3$. The organometallic agents, $R^5M$, may also be prepared from compounds $R^3H$ and a base in an inert solvent. Bases include, but are not limited to, alkali metal dialkylamides, preferably lithium di-isopropyl-amide, alkali metal bis(trialkylsilyl)amides, preferably lithium or sodium bis(trimethylsilyl)amides or alkyl lithiums, preferably n-butyl lithium or t-butyl lithium. Inert solvents include ethereal solvents, such as tetrahydrofuran or 1,2-dimethoxy-ethane, aromatic or non-aromatic hydrocarbons of 6 to 10 carbon atoms. Temperatures for the metallation and subsequent reaction range from −100° C. to 100° C., preferably −78° C. to 60° C.

Intermediates of Formula (II) may be prepared according to the following references, or by any combination of the general procedures described therein: S. Durand-Henchoz, R. C. Moreau, *Bull. Soc. Chim. Francais,* (1966), (11), 3416–3422; K. Murayama, S. Morimura, Y. Nakamura, G. Sunagawa, *Yakugaku Zasshi,* (1965), 85(2), 130–142; L. G. Rashidayan, G. T. Tatevosan, *Arm. Khim. Zh.,* (1970) , 23 (5) , 474–6 (*Chem. Abstracts,* (1970), 73, 130385u); S. M. McElvain, P. H. Parker, *J. Am. Chem. Soc.,* (1956), 78 5312; A. T. Babayan, K. Ts. Tagmazyan, L. P. Karapetyan, *Dokl. Akad. Nauk. Arm. SSR* (1975), 28(3), 244–9 (*Chem. Abstracts* (1975), 83, 79025g).

Compounds of Formula (III) (Formula I where $R^2$=OH) may be converted to compounds of Formula (IV), (Formula I where $R^2$=$O_2CR^{2a}$) using an appropriate acylating agent, $(R^{2a}CO)_2O$ or $R^{2a}COCl$. The acylation reaction may or may not employ a base. Bases which may be used for this reason include, but are not limited to, alkali metal hydrides, preferably sodium hydride, alkali metal carbonates, preferably potassium carbonate, alkali metal dialkylamides, preferably lithium di-isopropylamide, alkali bis(trialkyl-silyl)amides, preferably sodium bis(trimethylsilyl)amide, alkyl alkali metal compounds (such as n-butyl lithium), alkali metal alkoxides (such as sodium ethoxide), alkyl alkaline earth metal halides (such as methyl magnesium bromide), trialkylamines (such as triethylamine or di-isopropylethylamine) or polycyclic di-amines (such as, 1,4-diazabicyclo [2.2.2]octane or 1,8-diazabicyclo-[5.4.0]undecene). Alternatively, a dehydrating agent and a carboxylic acid of the Formula, $R^{2a}CO_2H$, may be reacted with a compound of Formula III. Dehydrating agents include, but are not limited to, dialkyl or dicycloalkyl carbodiimides (such as dicyclohexyl-carbodiimide), an alkyl chloroformate and a trialkylamine, carbonyldiimidazole. Such dehydrating agents are known in the general literature (see J. March, Advanced Organic Chemistry (New York: J. Wiley and Sons, 1985) pp. 348–351). Acylation procedures are also known in the general literature (see T. W. Greene, Protective Groups in Organic Synthesis (New York: J. Wiley and Sons, 1981) pp 50–64. The acylation procedures may use an inert solvent, compatible with the acylating agent or dehydrating agent as specified in the above March and Greene references or references cited therein. Inert solvents may include ethers such as tetrahydrofuran, halocarbons, such as dichloromethane, alkanes of 5 to 10 carbons, dialkylformamides of 3 to 10 carbons, dialkylacetamides of 4 to 16 carbons; cyclic tertiary amides such as N-methylpyrrolidone or aromatic amines such as pyridine.

Scheme II illustrates alternate methods to prepare some of the intermediates of Formula (II). Amides of Formula (V) (where $R^{21}$ is alkyl of 1 to 5 carbons, cycloalkyl of 3 to 6 carbons, cycloalkylalkyl of 4 to 7 carbons, phenyl-alkyl (1–5 carbons where the phenyl group is optionally substituted by $R^6$ and $R^7$, heteroaryl, naphthyl, heteroaryl-alkyl (1–5 carbons) or naphthyl-alkyl (1–5 carbons)) may be reacted with a reducing agent in the presence of an inert solvent to afford compounds of Formula (VI). Reducing agents may include, but are not limited to alkali metal aluminum hydrides, preferably lithium aluminum hydride, alkali metal trialkoxyaluminum hydrides (such as lithium tri-t-butoxyaluminum hydride), Scheme II

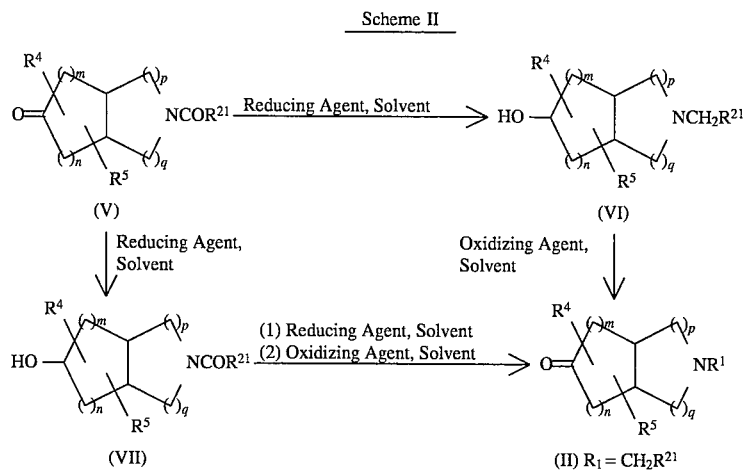

(V)    (VI)

(VII)    (II) $R_1$ = $CH_2R^{21}$ dialkylaluminum hydrides (such as di-isobutylaluminum hydride), borane, dialkylboranes (such as di-isoamyl borane), alkali metal trialkyl boron hydrides (such as lithium triethyl-boron hydride. Inert solvents include ethereal solvents (such as diethyl ether or tetrahydrofuran), aromatic or non-aromatic hydrocarbons of 6 to 10 carbons. Reaction temperatures for the reduction range from about −100° C. to 200° C., preferably −80° C. to 80° C. The choice of reducing agent and solvent is known to those skilled in the art as taught in the above cited March reference (pp 1093–1110). Compounds of Formula (VI) then may be treated with an oxidizing agent in an inert solvent to generate compounds of Formula II (where $R^1$=$CH_2$ $R^{21}$). Oxidizing agents may include transition metal oxides, such as $CrO_3$ or $MnO_2$, pyridine-chromium complexes, such as $CrO_3.C_5H_5N$, pyridinium dichromate or pyridinium chlorochromate, an oxalyl chloride-dimethyl sulfoxide-triethylamine reagent system, commonly called the Swern oxidation system (D. Swern et al., *J. Organic Chem.,* 43, 2480–2482 (1978)) or a dimethyl sulfoxide-dicyclohexylcarbodiimide system (see H. O. House, Modern Synthetic Reactions (New York: W. A. Benjamin Inc., 1972), pp. 416–421). Such oxidations may employ an inert solvent such as those in the reduction step described above or halocarbons of 1 to 6 carbons, preferably dichloromethane or 1,2-dichloroethane.

Alternatively, compounds of Formula V may be reacted with a reducing agent in an inert solvent to produce compounds of Formula VII. Reducing agents include alkali metal borohydrides, preferable sodium or lithium borohydride and alkali metal trialkoxyaluminum hydrides (such as lithium tri-t-butoxyaluminum hydride). Inert solvents include those used in the conversion of compounds of Formula V to those of Formula (VI) as well as hydroxyalkanes of 2 to 6 carbons. Compounds of Formula (VII) may then be converted by the reduction-oxidation sequence described above for the conversion of compounds

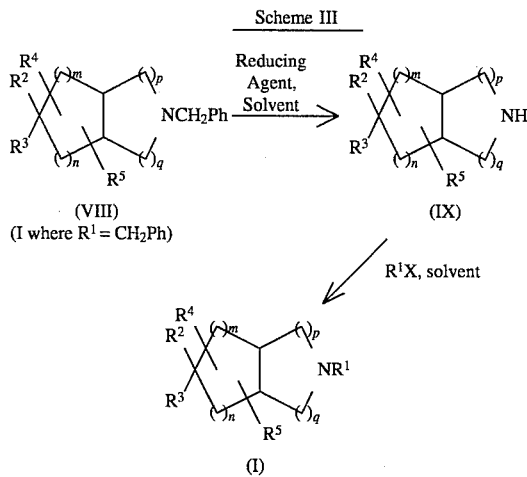

Scheme III (VIII) (I where $R^1$ = CH$_2$Ph)

(IX)

(I)

of Formula (V) to those of Formula (II) via intermediates of Formula (VI).

Intermediates of Formula (V) may be prepared according to the following references or by a combination of the general procedures described therein: R. L. Augustine, *J. Organic Chem.* 23, 1853–1856 (1958); S. Durand-Henchoz, R. C. Moreau, *Bull, Soc. Chim. Francais,* (11), 3416–3422 (1966).

Some of the compounds of Formula (I) may be also be prepared according to Scheme III. Compounds of Formula (VIII) (Formula I where $R^1$=CH$_2$Ph) may be reacted with a reducing agent in an inert solvent to give compounds of Formula IX (Formula (I) where $R^1$=H). Reducing agents may include molecular hydrogen and a noble metal catalyst, preferably palladium-on-carbon or platinum (IV) oxide, an ammonium formate-noble metal catalyst system (such as ammonium formate-palladium-on-carbon) (S. Ram, L. D. Spicer) *Tetrahedron Lett.,* 280 (5), 515–516 (1987)) or an alkali metal and liquid ammonia (preferably sodium and liquid ammonia) (see the above Green reference, pp 272–274). Inert solvents may include but are not limited to, lower alkyl alcohols, ethereal solvents such as diethyl ether or tetrahydrofuran or aromatic or non-aromatic hydrocarbons of 6 to 10 carbons. Intermediates of Formula (IX) may then be reacted with a compound, $R^1X$ where X may be Cl, Br, I, alkylsulfonyloxy (preferably methanesulfonyloxy), or haloalkylsulfonyloxy groups (preferably trifluoromethylsulfonyloxy), to generate compounds of Formula (I). A base may be required to effect the transformation from (IX) to (I). Bases may include alkali metal carbonates (such as potassium carbonate, trialkylamines, alkali metal hydrides (such as sodium hydride or quarternary ammonium salts (such as Triton B). The choice of solvent must be compatible with the base employed; solvents may include lower alkyl alcohols, ethereal solvents, lower alkyl nitriles or aromatic or non-aromatic hydrocarbons of 6 to 10 carbons. For a summary of the general procedures which may be employed, see the above March reference (pp 364–381).

Scheme IV

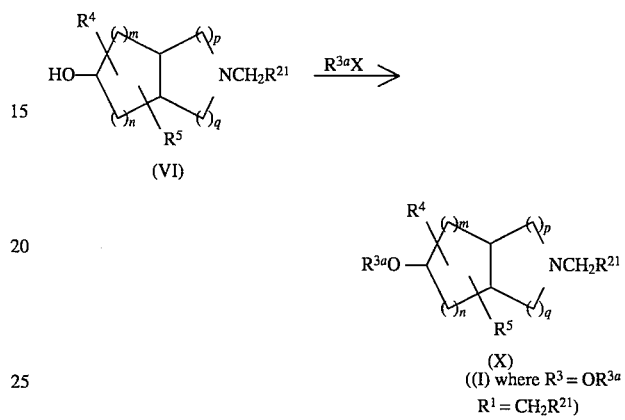

(VI)

(X) ((I) where $R^3$ = OR$^{3a}$ $R^1$ = CH$_2$R$^{21}$)

Some of the compounds of Formula (I) may be prepared according to Scheme IV. Compounds of Formula (VI) may be reacted with compounds of Formula $R^{3a}X$, where X may be defined as it was for $R^1X$ above in the conversion of compounds of Formula (VIII) to those of Formula (I). Similarly bases and inert solvents may be employed as they were in the conversion of (IX) to (I).

Some of the compounds of Formula I may also be prepared according to Scheme V. Compounds of Formula (VII) may be reacted with a sulfonylating agent, $R^{20}SO_2Cl$ or $(R_{20}SO_2)_2O$, (where $R^{20}$ is lower alkyl, substituted phenyl or lower haloalkyl), preferably methanesulfonylchloride, p-toluenesulfonyl chloride or trifluoro methanesulfonic anhydride, in the presence of a base, such as a trialkylamine, preferably triethylamine, an alkali metal hydride, preferably sodium hydride, an aromatic amine, preferably pyridine, or an alkali metal carbonate or alkoxide. Such a sulfonylation may be performed in an inert solvent such as a halocarbon of 1 to 6 carbons, preferably dichloromethane, ethereal solvents, such as diethyl ether or tetrahydrofuran, aromatic or non-aromatic hydrocarbons of 6 to 10 carbons or lower alkanenitriles, preferably acetonitrile. The sulfonylated intermediates of Formula (XI) are reacted with compounds of Formula $R^{3a}YH$ where Y=O or S. A base and an appropriate solvent may be used and may be drawn from the lists of bases and solvents described above for the transformation of (VI) to (X) above. Finally, compounds of Formula (XII) may be reacted with a reducing agent in an inert solvent to give compounds of Formula XIII (Formula I where $R^2$=H, $R^1$=CH$_2$R$^{21}$ $R^3$=R$^{3a}$Y, and Y=0, S. The choice of reducing agent follows that described above for the conversion of Compounds of Formula (V) to those of Formula (VI).

Scheme V

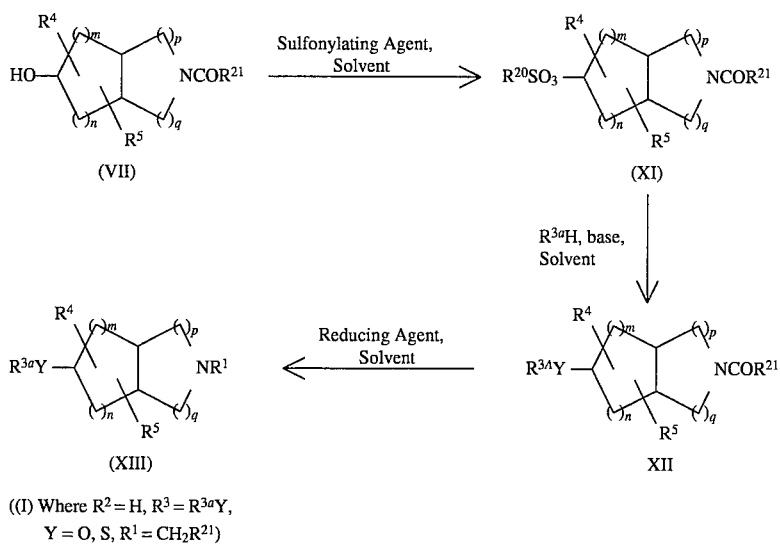

((I) Where $R^2 = H$, $R^3 = R^{3a}Y$,
$Y = O, S, R^1 = CH_2R^{21}$)

EXAMPLES

Analytical data were recorded for the compounds described below using the following general procedures. Infrared spectra were recorded on a Perkin-Elmer Model 1600 FT-IR spectrometer; absorbances are recorded in $cm^{-1}$ and intensities are denoted s (strong), m (moderate) and w (weak). Proton NMR spectra were recorded on a IBM-Bruker FT-NMR spectrometer (200 MHz or 300 MHz); chemical shifts were recorded in ppm ($\partial$) from an internal tetramethylsilane standard in deuterochloroform or deuterodimethylsulfoxide and coupling constants (J) are reported in HZ. Mass spectra (MS) or high resolution mass spectra (HRMS) were recorded on Finnegan MAT 8230 spectrometer or Hewlett Packard 5988A model spectrometer. Melting points were recorded on a Buchi Model 510 melting point apparatus and are uncorrected. Boiling points are uncorrected.

Reagents were purchased from commercial sources and, where necessary, purified prior to use according to the general procedures outlined by D. D. Perrin and W. L. F. Armarego, Purification of Laboratory Chemicals, 3rd ed., (New York: Pergamon Press, 1988). Chromatography was performed on silica gel using the solvent systems indicated below. For mixed solvent systems, the volume ratios are given. Parts and percentages are by weight unless otherwise specified. Common abbreviations include: THF (tetrahydrofuran), TBDMS (t-butyl-dimethylsilyl), DMF (dimethylformamide), Hz (hertz) TLC (thin layer chromatography).

EXAMPLE 1

Trans-2-Benzyl-6-hydroxydecahydroisoquinoline

Trans-2-Benzoyl-6-oxodecahydroisoquinoline (1.32 g, 0.51 mmol) was added portionwise to a stirred suspension of lithium aluminum hydride (0.78 g, 2.1 mmol) in amhydrous THF (20 mL). The reaction mixture was heated to reflux under a nitrogen atmosphere and stirred for 18 hr. After being cooled to ambient temperature, the reaction was quenched with excess ethyl acetate, followed by water (1 mL), a 2N NaOH solution (1 mL) and water (3 mL). The suspension was filtered through Celite; the filtrate was dried over magnesium sulfate, filtered and concentrated in vacuo. Column chromatography (ethyl acetate) gave the product, a solid (560 mg): mp 90°–91° C.; NMR (CDCl$_3$, 200 MH$_z$): 7.4–7.25 (m, 5H), 3.7–3.5 (m, 1H), 3.5 (s, 2H), 3.0–2.75 (m, 2H), 2.1–0.9 (m, 14H); HRMS: Calcd: 245.1780, Found: 245.1783.

EXAMPLE 2

Cis-2-Benzyl-6-hydroxydecahydroisoquinoline

Following the procedure of Example 1, cis-2-benzoyl-6-oxodecahydroisoquinoline (20.4 g, 79.4 mmol) and lithium aluminum hydride (22 g, 578 mmol) were reacted in anhydrous THF (1100 mL) to give the product (17.6 g), an oil:NMR(CDCl13, 300 MHz): 7.35–7.15 (m, 5H), 3.9–3.3 (m, 2H), 3.5 (s, 2H), 2.7–2.5 (m, 2H), 2.5–1.2 (m, 12H); MS=245.

EXAMPLE 3

Cis-2-Benzyl-6-oxodecahydroisoquinoline

Oxalyl chloride (12.2 g, 8.4 mL, 96 mmol) and dichloromethane (200 mL) were stirred at –78° C. under a nitrogen atmosphere in a flame-dried flask. A solution of dimethylsulfoxide (15.0 g, 13.6 mL, 192 mmol) in dichloromethane (200 mL) was added dropwise over 20 min. The reaction mixture was stirred at –78° C. for 15 min. A solution of cis-2-benzyl-6-hydroxydecahydroisoquinoline (Example 2, 17.6 g, 71.8 mmol) in dichloromethane (300 mL) was added dropwise over 15 min. The reaction mixture was warmed to –65° C., stirred for 15 min, and cooled to –78° C. Triethylamine (26.9 g, 37 mL, 266 mol) was added in one portion and the reaction mixture was then warmed gradually to room temperature and stirred for 38.5 h. The reaction mixture was poured onto water and mixed. The layers were separated; the organic layer was washed twice with water. Drying over magnesium sulfate, filtration and removal of solvent in vacuo gave an oil. Column chromatography, (chloroform-:methanol:9:1) afforded the product, an oil (10.0 g): NMR (CDCl$_3$, 300 MHz): 7.35–7.2 (m, 5H), 3.45 (dd, 2H, J=15, 8), 2.8–2.65 (m, 2H), 2.55–2.05 (m, 8H), 1.85–1.75 (m, 1H), 1.65–1.45 (m, 2H); CMR (CDCl$_3$, 75.4 MHz): 211.6, 138.8, 128.5, 128.1, 126.8, 62.9, 56.7, 53.0, 45.7, 40.0, 37.0, 34.8, 27.8, 26.8; MS:243.

An additional 2.4 g of impure product was obtained, which was rechromatographed to give 695 mg of pure product.

EXAMPLE 4

Trans-2-Benzyl-6-oxodecahydroisoquinoline

Following the procedure described in Example 3, trans-2-benzyl-6-hydroxydecahydroisoquinoline (12.5 g, 51 mmol), oxalyl chloride (8.6 g, 5.9 mL, 68 mmol), dimethyl sulfoxide (10.6 g, 9.7 mL, 136 mmol) and triethylamine (19.0 g, 26.2 mL, 188 mmol) were reacted in dichloromethane (500 mL) to give the product, an oil (10.0 g): NMR (CDCl$_3$, 300 MHz): 7:35–7.25 (m, 5H), 3.55 (dd, 2H, J=10, 8), 2.9 (br d, 2H, J=8), 2.45–2.3 (m, 3H), 2.15–1.85 (m, 3H), 1.75–1.25 (m, 6H); CMR (CDCl$_3$, 75.4 MHz): 210.6, 138.3, 128.9, 128.1, 126.9, 63.1, 58.9, 53.2, 47.6, 41.5, 40.9, 40.1, 33.0, 30.1; MS:243.

EXAMPLE 5

Trans-2-Benzoyl-6-hydroxydecahydroisoquinoline

A mixture of trans-2-benzoyl-6-oxodecahydroisoquinoline (4.0 g, 29.1 mmol) and sodium borohydride (3.78 g, 100 mmol) in ethanol (200 mL) was stirred at ambient temperature for 28 h under a nitrogen atmosphere. The reaction mixture was concentrated in vacuo. The residue was taken up in a 1N NaOH solution, mixed and extracted three times with ethyl acetate. The combined organic layers were washed once with brine, dried over magnesium sulfate and filtered. Solvent was removed in vacuo to afford a white solid (2.8 g) which was homogeneous by TLC:mp 122°–124° C.; NMR (CDCl$_3$, 300 MHz): 7.5–7.3 (m, 5H), 4.9–4.6 (m, 1H), 3.85–3.6 (m, 2H), 3.1–2.9 (m, 1H), 2.8–2.55 (m, 1H), 2.45–2.25 (m, 1H), 2.2–0.9 (m, 10M), MS:259.

EXAMPLE 6

Cis-2-Benzoyl-6-hydroxydecahydroisoquinoline

Following the procedure described for Example 5, cis-2-benzoyl-6-oxodecahydroisoquinoline (1.7 g, 6.6 mmol) and sodium borohydride were reacted in ethanol (50 mL) to give the product (1.36 g): NMR (CDCl$_3$, 300 MHz): 7.4–7.3 (m, 5H), 4.85–4.6 (m, 1H), 3.85–3.5 (m, 2M), 3.1–2.9 (m, 1H), 2.75–2.5 (m, 1H), 2.5–2.2 (m, 1H), 2.1–0.9 (m, 10M); MS:259.

EXAMPLE 7

Cis-2-Benzyl-6-(4'-fluorophenyl)-6-hydroxydecahydro isoquinoline

A solution of cis-2-benzoyl-6-(4'-fluorophenyl)- 6-hydroxydecahydroisoquinoline (478 mg, 1.35 mmol) in anhydrous tetrahydrofuran (10 mL) was added dropwise to a stirred suspension of lithium aluminum hydride (95%, 0.31 g, 8.12 mmol) in anhydrous tetrahydrofuran (10 mL) under a nitrogen atmosphere. The reaction mixture was then heated to reflux temperature and stirred for 23 h. After the reaction was cooled to room temperature, an excess amount of ethyl acetate was added with stirring. Water (0.3 mL), a 2N NaOH solution (0.3 mL) and water (1 mL) were added in order. The mixture was filtered through Celite. The filtrate was dried over magnesium sulfate, filtered and concentrated in vacuo.

Column chromatography (CHCl$_3$:MeOH::9:1) gave the product (187 mg, 41% yield):NMR(CDCl$_3$, 200 MHz): 7.45 (dd, 2H, J=8,6), 7.4–7.2 (m, 5H), 7.0 (t, 2H, J=7), 3.5 (dd, 2H, J=14,7), 2.8–2.6 (m, 2H), 2.4–1.4 (m, 13H); HRMS: Calcd: 339.1999; Found:339.1998; Anal. Calcd. for C$_{22}$H$_{26}$FNO.0.2H$_2$O: C, 77.03, H, 7.76, N, 4.08; Found: C, 77.16, 77.18, H, 7.53, 7.62, N, 4.15, 4.21.

EXAMPLE 8

Cis-2-Benzyl-6-(4'-fluorophenyl)-6-hydroxydecahydro isoquinoline

A mixture of cis-2-benzyl-6-oxo decahydroisoquinoline (1.23 g, 5.1 mmol), p-fluorophenylmagnesium bromide (1M in THF, 10 mL, 10 mmol) and anhydrous THF (25 mL) was stirred under a nitrogen atmosphere for 15 h. The reaction mixture was poured onto a saturated ammonium chloride solution, mixed, basified with a 1N NaOH solution and extracted with ethyl acetate three times. Drying of the combined organic layers over magnesium sulfate, filtration and removal of solvent in vacuo gave an oil.

Column chromatography (CHCl$_3$:MeOH::9:1) gave the product (1.1 g, 64% yield) which was identical to Example 7: mp 106°–108° C.

EXAMPLE 9

Cis-2-Phenethyl-6-(4'-fluorophenyl)-6-hydroxy-decahydroisoquinoline

Part A: Nitrogen gas was bubbled through methanol (25 mL). The following reagents were added in order: 10% palladium on carbon (0.5 g), the product of Example 8 (0.5 g, 1.5 mmol) and ammonium formate (1.0 g). The reaction mixture was heated to reflux temperature and stirred for 30 min. The reaction mixture was cooled to ambient temperature and filtered through Celite. The filter pad was washed with methanol and chloroform. The combined filtrates were concentrated in vacuo. The residue was treated with a 1N NaOH solution and extracted three times with ethylacetate. The combined organic layers were dried over magnesium sulfate and filtered. Solvent was removed in vacuo to give cis- 6-(4'-fluorophenyl)-6-hydroxydecahydroisoquinoline: NMR (CDCl$_3$, 300 MHz): 7.45 (dd, 2H, J=8, 6), 7.0 (t, 2H, J=8), 3.15–1.4 (m, 16H); HRMS: Calcd: 249. 1529 Found: 249.1531.

Part B: The crude product from Part A was dissolved in anhydrous THF (10 mL). Phenethyl bromide (0.37 g, 2 mmol) and triethylamine (1.01 g, 1.4 mL, 10 mmol) were added. The reaction mixture was heated to reflux temperature and stirred for 13.5 h. The reaction mixture was cooled to room temperature, poured onto a 1N NaOH solution, mixed and extracted three times with ethyl acetate. The combined organic layers were dried over magnesium sulfate, filtered and concentrated in vacuo.

Column chromatography (CHCl$_3$:MeOH::9:1) gave two fractions: (1) the less polar isomer of the product, a white solid (R$_f$=0.2, 278 mg): mp 166°–169° C. (dec); NMR (CDCl$_3$, 300 MHz): 7.5 (dd, 2H, J=8, 6), 7.35–7.15 (m, 5H), 7.0 (t, 2H, J=8), 2.9–1.5 (m, 17H); MS:353; Anal. Calcd for C$_{23}$H28FNO.H$_2$O:C, 74.36, H, 8.14, N, 3.77, Found: C, 74.82, 74.76, H, 7.65, 7.77, N, 3.52, 3.59; (2) the more polar isomer of the product, an oil (R$_f$=0.15, 104 mg):

NMR(CDCl$_3$, 300 MHz): 7.5 (dd, H, J=8, 6), 7.35–7.15 (m, 5H), 7.05 (t, 2H, J=8), 2.9–1.4 (m, 17H); MS:353.

EXAMPLES 10 TO 16

Examples 10 to 16 were prepared according the general procedure of Example 9.

TABLE 1

[Structure: trans-decahydroisoquinoline with 4-fluorophenyl and OH at one position, NR substituent, with H stereochemistry markers]

| Example | R | mp (°C.) |
|---|---|---|
| 10 | 2-(4'-fluorophenyl)ethyl | 161–163[a] |
| 11 | 2-(4'-methoxyphenyl)ethyl | 168–169[b] |
| 12 | cyclohexylmethyl | 48–49[c] |
| 13 | 2-naphthylmethyl | 56–57[d] |
| 14 | 2-(3-indolyl)ethyl | 204–206(dec)[e] |
| 15 | 4-pyridylmethyl | 116–118[f] |
| 16 | 4-nitrobenzyl | 208[g] |

Footnotes to Table 1:
[a]NMR (CDCl$_3$, 300 MHz): 7.5(dd, 2H, J=8, 6), 7.25(dd, 2H, J=8, 6), 7.2–7.0(m, 4H), 3.35(s, 1H), 3.35(d, 1H, J=7), 2.85–2.7(m, 2H), 2.55–1.6(m, 14H), 1.4–1.2(m, 1H); HRMS: Calcd: 371.2061, Found: 371.2054; Anal. Calcd for C$_{23}$H$_{27}$F$_2$NO.H$_2$O: C, 70.93, H, 7.51, N, 3.60, F, 9.75. Found: C, 71.14, 71.01, H, 7.17, 7.17, N, 3.65, 3.69, F, 9.40, 9.30.
[b]NMR (CDCl$_3$, 300 MHz): 7.45(dd, 2H, J=8, 6), 7.15(d, 2H, J=7), 7.0(t, 2H, J=8), 6.85(d, 2H, J=7), 3.8(s, 3H), 2.9–1.4(m, 19H); MS: 383; Anal. Calcd for C$_{24}$H$_{30}$FNO$_2$.1.2H$_2$O: C, 71.15, H, 8.06, N, 3.45, F, 4.68; Found: C, 71.11, 70.82, H, 7.60, 7.53, N, 3.65, 3.79, F, 5.06.
[c]NMR (CDCl$_3$, 300 MHz): 7.5(dd, 2H, J=8.6), 7.05–6.95(m, 2H), 2.85–1.1(m, 26H), 1.0–0.8(m, 2H); HRMS: Calcd: 345.2468, Found: 345.2467; Anal. Calcd for C$_{22}$H$_{32}$FNO.0.75H$_2$O: C, 73.60, H, 9.41, N, 3.90, Found: C, 73.90, 73.81, H, 9.13, 9.21, N, 3.87, 3.88.
[d]NMR (CDCl$_3$, 300 MHz): 7.9–7.7(m, 4H), 7.6–7.4(m, 5H), 7.1–6.95(m, 2H), 3.8–3.55(m, 2H), 2.9–1.4(m, 14H); HRMS: Calcd: 389.2155, Found: 389.2158; Anal. Calcd for C$_{26}$H$_{29}$FNO.0.75H$_2$O: C, 77.48, H, 7.37, N, 3.47, Found: C, 77.94, 77.82, H, 7.11, 7.10, N, 3.27, 3.28.
[e]NMR (CDCl$_3$, 300 MHz): 11.1–10.7(m, 1H), 7.7–6.95(m, 9H), 3.9–3.75(m, 2H), 3.4–2.8(m, 8H), HRMS: Calcd: 392.2264, Found: 392.2267; Anal. Calcd. for C$_{25}$H$_{29}$FN$_2$O.3H$_2$O: C, 67.24, H, 6.55, N, 6.27, F, 4.25; Found: C, 66.85, 66.82, H, 6.59, 6.42, N, 6.09, 6.06, F, 3.06, 3.11.
[f]NMR (CDCl$_3$, 300 MHz): 8.5(d, 2H, J=6), 7.5(dd, 2H, J=8,6), 7.3(d, 2H, J=6), 7.05(t, 2H, J=8), 3.5(d, 1H, J=12), 3.4(d, 1H, J=12), 2.8–1.4(m, 15H); HRMS: Calcd: 340.1951, Found: 340.1957; Anal. Calcd for C$_{21}$H$_{25}$FN$_2$O.0.6H$_2$O, C, 71.81, H, 7.51, H, 7.97, F, 5.41; Found: C, 71.69, 71.82, H, 7.18, 7.68, N, 7.66, 7.60, F, 5.15, 5.12.
[g]NMR (CDCl$_3$, 300 MHz): 8.15(d, 2H, J=8), 7.55–7.45(m, 4H), 7.05(t, 2H, J=8), 3.55(g, 2H J=30,15), 2.8–2.6(m, 2H), 2.5–1.7(m, 9H), 1.7–1.4(m, 4H); MS: 384; Anal. Calcd for C$_{22}$H$_{25}$FN$_2$O$_3$: C, 68.73, H, 6.55, N, 7.29, F, 4.94, Found: C, 68.33, H, 6.55, N, 7.02, F, 4.88.

EXAMPLE 17

Trans-2-Benzyl-6-(4'-fluorophenyl)-6-hydroxy-decahydroisoquinoline

A solution of trans-2-benzoyl-6-(4'-fluorophenyl)- 6-hydroxydecahydroisoquinolone (76 mg, 2.16 mmol) in anhydrous THF (20 mL) was added dropwise to a stirred suspension of lithium aluminum hydride (95%, 0.49 g, 12.9 mmol) in anhydrous THF (20 mL) under a nitrogen atmosphere. The reaction mixture was then heated to reflux temperature and stirred for 23.5 h. The reaction was cooled to ambient temperature, quenched with an excess amount of ethyl acetate, followed by water (0.5 mL), a 2N NaOH solution (0.5 mL) and water (1.5 mL). The mixture was filtered through Celite. The filtrate was dried over magnesium sulfate, filtered and concentrated in vacuo. Column chromatography (ethyl acetate or CHCl$_3$::MeOH::9:1) gave the product, a solid (382 mg): mp 120°–122° C.; NMR (CDCl$_3$, 300 MHz): 7.45 (2H, dd, J=8, 6), 7.4–7.2 (m, 5H), 7.0 (br t, 2H, J=7), 3.55 (s, 2H), 2.95 (br d, 1H, J=7), 2.85 (br d, 1H, J=7), 2.05 (br t, 1H, J=7), 1.9–1.2 (m, 12H); HRMS: Calcd: 339.1999, Found: 339.2001; Anal. Calcd for C$_{22}$H$_{26}$FNO: C, 77.84, H, 7.72, N, 4.13, F, 5.60, Found: C, 77.41, 77.16, H, 7.74, N, 4.19 3.97, F, 5.78.

EXAMPLE 18

Trans-2-Benzyl-6(4'-fluorophenyl)-6-hydroxy-decahydroisoquinoline

A solution of trans-2-benzyl-6-oxodecahydroisoquinoline (5.4 g, 22.2 mmol) and p-fluorophenylmagnesium bromide (1M in THF, 33 mL, 33 mmol) in anhydrous THF (100 mL) was stirred at room temperature under a nitrogen atmosphere for 22 h. The reaction was poured onto a saturated ammonium chloride solution, mixed, basified with a 1N NaOH solution and extracted three times with ethyl acetate. The combined organic layers were dried over MgSO$_4$, filtered and concentrated in vacuo. Column chromatography (ethyl acetate) gave the product a solid (2.83 g), which was identical to the product of Example 17.

EXAMPLE 19

Trans-6-(4'-fluorophenyl)-6-hydroxydeca-hydroisoquinoline

Following the general procedure described in Example 9, Part A, the product of Example 18 (1.0 g, 2.9 mmol), 10% palladium on charcoal (1.0 g), and ammonium formate (2 g) were reacted in methanol (75 mL) to afford the product, a white solid (0.6 g): mp 174°–175° C.; NMR (CDCl$_3$, 300 MHz): 7.5–7.4 (m, 2H), 7.1–6.9 (m, 2H), 3.2–3.0 (m, 2H), 2.8–2.6 (m, 1H), 2.4–2.3 (m, 1H), 2.0–1.0 (m, 25H); MS:249; Anal. Calcd for C$_{15}$H$_{20}$FNO.3H$_2$O:C, 70.73, H, 8.23, N, 5.50, F, 7.45; Found: C, 70.82, 70.89, H, 8.10, 8.04, N, 5.14, 5.20, F, 7.08, 6.92.

EXAMPLES 20 TO 22

Examples 20 to 22 were prepared according to the general procedure described for Example 9, Part B. In some cases, potassium carbonate in refluxing ethanol may be substituted for triethylamine in refluxing THF.

TABLE 2

[Structure: trans-decahydroisoquinoline with 4-fluorophenyl, OH, NR substituent]

| Example | R | mp (°C.) |
|---|---|---|
| 20 | cyclopropylmethyl | 155–156 (a) |
| 21 | 4-t-butylbenzyl | 62–63 |
| 22 | allyl | 150 (c) |

Footnotes for Table 2:

TABLE 2-continued

[Structure: decahydroisoquinoline with 4-fluorophenyl and OH substituents, NR group, with H stereochemistry indicators]

Example    R    mp (°C.)

(a) NMR (CDCl₃, 200 MHz): 7.5(dd, 2H, J=8, 6), 7.05(t, 2H, J=8), 3.3(br d, 1H, J=10), 3.15(br d, 1H, J=10), 2.45(d, 2H, J=7), 2.3–2.1(m, 1H), 2.0–1.7(m, 3H), 1.7–1.45(m, 7H), 1.35–1.2(m, 1H), 1.05–0.9(m, 2H), 0.65–0.5(m, 2H), 0.25–0.1(m, 2H); HRMS: Calcd: 303.1999, Found: 303.2002; Anal. Calcd for $C_{19}H_{26}FNO \cdot 0.6H_2O$: C, 72.63, H, 8.70, N, 4.45, F, 6.05, Found: C, 72.42, 72.50, H, 8.87, 8.79, N, 4.27, 4.33, F, 4.99, 4.95.
(b) NMR (CDCl₃, 300 MHz): 7.5(dd, 2H, J=8, 6), 7.3(d, 2H, J=8), 7.2(d, 2H, J=8), 7.05(t, 2H, J=8), 3.45(br s, 2H), 2.9(br d, 1H, J=8), 2.8(br d, 1H, J=8), 2.55–2.45(m, 1H), 2.45–2.3(m, 1H), 2.0–1.4(m, 9H), 1.3(s, 9H), 1.1–0.8(m, 2H), MS: 395; Anal. Calcd for $C_{26}H_{34}FNO \cdot 0.75H_2O$: C, 76.34, H, 8.74, N, 3.42, F, 4.64, Found, C, 76.66, 76.54, H, 8.49, 8.42, N, 3.24, 3.21, F, 3.88, 3.88.
(c) NMR (CDCl₃, 300 MHz): 7.45(dd, 2H, J=8, 6), 7.0(t, 2H, J=8), 6.0–5.8(m, 1H), 5.2(t, 2H, J=7), 3.1–2.8(m, 4H), 2.1–1.2(m, 14H); MS: 289; Anal. Calcd for $C_{18}H_{24}FNO \cdot 0.75H_2O$: C, 71.37, H, 8.41, N, 4.62, F, 6.27, Found: C, 71.37, H, 8.13, N, 4.49, F, 5.93.

EXAMPLE 23

Trans-2-(4'-(4''-fluorophenyl)-4',4'-ethylenedioxy)butyl-6-(4'''-fluorophenyl)-6-hydroxydecahydroisoquinoline A mixture of the product from Example 19 (0.55 g, 2.2 mmol), 4-chloro-1-(4'-fluorophenyl) butyrophenone ethylene glycol ketal (0.75 g, 3 mmol), potassium iodide (0.83 g, 5 mmol) and potassium carbonate (0.7 g, 5 mmol) in DMF (10 mL) was stirred at reflux temperature under a nitrogen atmosphere for 16 h. The reaction mixed was cooled to ambient temperature. The solvent was distilled in vacuo. The residue was taken up in a 1N NaOH solution, mixed and extracted with ethyl acetate three times. The combined organic layers were dried over magnesium sulfate, filtered and concentrated in vacuo. Column chromatography (CHCl₃:MeOH::9:1) gave the product, an oil (1 g): NMR (CDCl₃, 300 MHz): 7.45 (dd, 2H, J=8, 6), 7.35 (dd, 2H, J=8, 6), 7.1–6.9 (m, 4H), 4.1–3.9 (m, 2H), 3.8–3.6 (m, 2H), 2.9 (br d, 1H, J=10), 2.8 (d, 1H, J=10), 2.5 (dd, 1H, J=10, 2), 2.4–2.2 (m, 2H), 1.95–1.7 (m, 4H), 1.7–1.35 (m, 9H), 1.05–0.75 (m, H); MS:457.

EXAMPLE 24

Trans-2-(4'-(4''-fluorophenyl)-4'-oxobutyl)-6-(4'''-fluorophenyl)-6-hydroxydecahydroisoquinoline The product of Example 23 (1 g), concentrated hydrochloric acid (2 mL), water (4 mL) and THF were mixed and stirred for 24 h. The reaction mixture was poured onto a 1N NaOH solution, mixed and extracted three times with ethyl acetate. The combined organic layers were dried over magnesium sulfate, filtered and concentrated in vacuo. Column chromatography (CHCl₃:MeOH::9:1) afforded the product, a solid (450 mg):mp 160° C.; NMR (CDCl₃, 300 MHz):8.0 (dd, 2H, J=8, 6), 7.5 (dd, 2H, J=8, 6), 7.15 (t, 2H, J=8), 7.05 (t, 2H, J=8), 3.25–2.9 (m, 4H), 2.7–2.5 (m, 2H), 2.3–1.2 (m, 15H); MS:413; Anal. Calcd for $C_{25}H_{29}F_2NO_2 \cdot 1.5H_2O$:C, 68.16, H, 7.32, N, 3.17, F, 8.63; Found: C, 67.94, 67.92, H, 6.95, 6.93, N, 2.96, 3.11, F, 7.12, 7.09.

EXAMPLE 25

Trans-2-Benzoyl-6-(4'-fluorophenyl)-6-hydroxydecahydroisoquinoline

A solution of trans-2-benzoyl-6-oxodecahydroisoquinoline (2.0 g, 7.8 mmol) in anhydrous THF was cooled to –78° C. with stirring under a nitrogen atmosphere. A solution of p-fluorophenylmagnesium, bromide in THF (1.0M, 7.8 mL, 7.8 mmol) was added dropwise. The reaction mixture was stirred at –78° C. for 3 h, then warmed to room temperature over 16 h. The reaction mixture was poured onto a saturated ammonium chloride solution, mixed, basified with 1N NaOH solution and extracted with ethyl acetate three times. The combined organic layers were dried over magnesium sulfate, filtered and concentrated in vacuo. Column chromatography (ethyl acetate) afforded: (1) the less polar hydroxyl epimer of the entitled product ($R_f$=0.52, 934 mg): mp 107°–108° C.; NMR (CDCl₃, 300 MHz) 7.5–7.3(m, 7H), 7.05 (t,2H, J=7), 4.9–4.7 (m, 1H), 3.9–3.65 (m, 1H), 1.9–1.1 (m, 10H); CMR (CDCl₃, 68 MHz): 170.2, 161.5 (d, J=245), 144.9, 136.1, 129.4, 128.3, 126.7, 126.1 (d, J=8), 114.7 (d, J=21), 72.9, 53.4, 48.4, 47.7, 45.0, 42.8, 41.9, 40.9, 38.0, 36.8, 32.9, 31.9, 25.3; HRMS:Calcd:353.1791, Found:353.1791; (2) a mixture of hydroxyl epimers of the entitled product (184 mg) and (3) the more polar hydroxyl epimer of the entitled product, an oil ($R_f$=0.41, 302 mg): NMR (CDCl₃, 300 MHz): 7.55–7.3 (m, 7H), 7.05 (t, 2H, J=7), 4.9–4.6 (m, 1H), 3.9–3.6 (m, 1H), 3.1–1.0 (m, 13H); CMR (CDCl₃, 68 MHz): 170.0, 166.8 (d, J=246), 135.8 (d, J=17), 129.4 (d, J=14), 128.3, 128.2, 128.1, 128.0, 126.7, 126.6, 115.0 (d, J=21), 72.4, 47.1, 44.8, 42.3, 41.6, 37.4; HRMS: Calcd 353.1791; Found:353.1791.

EXAMPLE 26

Cis-2-Benzoyl-6-(4'-fluorophenyl)-6-hydroxydecahydroisoquinoline

Following the general procedure described in Example 25, a solution of p-fluorophenyl magnesium bromide in THF (1.0M, 2.61 mL, 2.61 mmol) was reacted with cis-2-benzoyl-6-oxodecahydroisoquinoline (670 mg, 2.61 mmol) in anhydrous THF at –78° C. Column chromatography (ethyl acetate) afforded the product, a solid (478 mg):mp 84°–85° C.; NMR (CDCl₃, 200 MHz): 7.5–7.35 (m, 7H), 7.0 (t, 2H, J=8), 4.65–4.35 (m, 1H), 3.8–3.6 (m, 1H), 3.3–3.1 (m, 1H), 3.1–2.8 (m, 1H), 2.65–2.35 (m, 1H), 2.1–1.4 (m, 10 H); Anal. Calcd for $C_{22}H_{24}FNO_2$: C, 74.76, H, 6.84, N, 3.96, F, 5.38; Found: C, 74.59, H, 6.93, N, 3.79, F, 5.53.

EXAMPLE 27

Trans-2-Benzyl-6-(4'-fluorophenyl)-6-hydroxydecahydroisoquinoline (hydroxyl epimer A)

The less polar hydroxyl epimer of Example 25 (934 mg, 2.65 mmol), lithium aluminum hydride (0.63 g, 15.9 mmol) and anhydrous THF (30 mL) were stirred at reflux temperature under a nitrogen atmosphere for 17 h. The reaction mixture was cooled to ambient temperature and quenched successively with excess ethyl acetate, water (0.6 mL), a 1N NaOH solution (0.6 mL). The mixture was filtered through Celite and the filtrate was dried over magnesium sulfate and filtered. Solvent was removed in vacuo to give a solid (700 mg):NMR (CDCl₃, 200 MHz): 7.45 (dd, 2H, J=8, 6), 7.35–7.2 (m, 5H), 7.0 (t, 2H, J=8), 3.5 (s, 2H), 2.95 (br d, 1H, J=10), 2.85 (br d, 1H, J=10), 2.05 (td, 1H, J=7, 1), 1.85–1.25 (m, 12H).

EXAMPLE 28

Trans-2-Benzyl-6-(4'-fluorophenyl)-6-hydroxydecahydroisoquinoline (hydroxyl epimer B)

Following the procedure of Example 26, the more polar epimer of Example 25 (302 mg, 0.86 mmol) was reacted with lithium aluminum hydride (0.2 g, 5.16 mmol) in anhydrous THF (10 mL) to give the product, an oil (262 mg): NMR (CDCl$_3$, 200 MHz): 7.5 (dd, 2H, J=8, 6), 7.4–7.2 (m, 5H), 7.05 (t, 2H, J=8), 3.7–3.5 (m, 1H), 3.45 (d, 1H, J=10), 3.35 (d, 1H, J=10), 2.95–2.7 (m, 2H), 2.5 (br d, 1H, J=12), 2.35 (br d, 1H, J=12), 2.05–0.8 (m, 12H).

EXAMPLE 29

Trans-2-Benzyl-6-(4'-fluorophenyl)-6-hydroxydecahydroisoquinoline (hydroxyl epimer A)

A solution of p-fluorophenylmagnesium bromide in THF (1M, 33 mL, 33 mmol) was added dropwise to a solution of trans-2-benzyl-6-oxodecahydroisoquinoline with stirring. After being stirred for 22 h, the reaction mixture was poured onto a saturated ammonium chloride solution, mixed basified with a 1N NaOH solution and extracted three times with ethyl acetate. The combined organic layers were dried over magnesium sulfate, filtered and concentrated in vacuo. Column chromatography (ethyl acetate) afforded the product, a solid (2.83 g): NMR (CDCl$_3$, 300 MHz): 7.45 (dd, 2H, J=8, 6), 7.35–7.2 (m, 5H), 7.0 (t, 2H, J=8), 3.5 (s, 2H), 2.95 (br d, 1H, J=10), 2.85 (br d, 1H, J=10), 2.05 (td, 1H, J=7, 1), 1.85–1.25 (m, 12H); CMR (CDCl$_3$, 75.4 MHz): 163.2, 160.0, 145.0, 138.4, 129.1, 128.1, 126.8, 126.1, 126.0, 114.9, 114.6, 73.4, 63.3, 59.6, 54.1, 45.3, 40.9, 38.4, 38.6, 32.4, 26.0; HRMS: Calcd: 339.1999, Found: 339.2015.

EXAMPLES 30 TO 42

Examples 30 to 42 were prepared following the procedure of Example 8, using the appropriate reagent and cis-2-benzyl-6-oxodecahydroisoquinoline.

TABLE 3

| Example | R | mp (°C.) |
|---|---|---|
| 30 | 4-methoxyphenyl | 108–109 (a) |
| 31 | 4-methylthiophenyl | 107–109 (b) |
| 32 | 4-t-butylphenyl | 106–107 (c) |
| 33 | 4-biphenyl | 114–115 (d) |
| 34 | t-butyl | (e) |
| 35 | 2-naphthyl | 136–138 (f) |
| 36 | allyl | (g) |
| 37 | 2-thienyl | 101–104 (h) |
| 38 | cyclohexyl | 63–66 (i) |
| 39 | CH$_3$ | (j) |
| 40 | 2-furyl | (k) |
| 41 | phenyl | (l) |
| 42 | benzyl | (m) |

Footnotes to Table 3:
(a) NMR CDCl$_3$, 300 MHz): 7.45(d, 2H, J=7), 7.4–7.2(m, 5H), 6.9(d, 2H, J=7), 3.85(s, 3H), 2.6–2.4(m, 2H), 2.95–1.4(m, 15H); HRMS: Calcd: 351.2198, Found: 351.2200; Anal. Calcd for C$_{23}$H$_{29}$NO$_2$.0.4H$_2$O: c, 77.01, H, 8.37, N, 3.91, Found: C, 76.89, 77.01, H, 8.20, 8.25, N, 3.48, 3.60.

TABLE 3-continued (b) NMR (CDCl$_3$, 300 MHz): 7.45(d, 2H, J=7), 7.35–7.2(m, 7H), 3.5(dd, 2H, J=14, 7), 2.8–2.6(m, 2H), 2.5(s, 3H), 2.3–1.4(m, 13H); HRMS: Calcd: 367.1970, Found: 367.1980; Anal. Calcd for C$_{23}$H$_{29}$NOS.0.25H$_2$O: C, 74.25, H, 7.99, N, 3.76, Found: C, 74.40, 74.34, H, 7.86, 7.77, N, 3.55, 3.56.
(c) NMR (CDCl$_3$, 300 MHz): 7.5–7.2(m, 9H), 3.6–3.4(m, 2H), 2.8–2.6(m, 2H), 2.4–1.4(m, 13H), 1.3(s, 9H); HRMS: Calcd: 377.2719, Found: 377.2720; Anal. Calcd for C$_{26}$H$_{35}$NO − 0.25H$_2$O: C, 81.73, H, 9.36, N, 3.66; Found: C, 81.83, 81.58, H, 9.34, 9.26, N, 3.41, 3.50.
(d) NMR (CDCl$_3$, 300 MHz): 7.6–7.2(m, 14H), 3.5(dd, 2H, J=14, 10), 2.8–2.6(m, 12H) 2.5–1.4(m, 12H); HRMS: Calcd: 397.2406, Found: 397.2407; Anal. Calcd for C$_{28}$H$_{31}$NO: C, 84.59, H, 7.86, N, 3.52; Found: C, 84.44, H, 7.63, N, 3.25.
(e) NMR (CDCl$_3$, 300 MHz): 7.4–7.1(m, 5H), 3.45(dd, 2H, J=37,8), 2.95–2.8(m, 1H), 2.7(d, 1H, J=8), 2.55–1.2(m, 10H), 0.9(s, 9H), 1.05–0.8(m, 1H); MS: 301.
(f) NMR (CDCl$_3$, 300 MHz): 8.0–7.8(m, 4H), 7.6–7.2(m, 8H), 3.6–3.4(m, 2H), 2.8–1.4(m, 20H); Anal. Calcd for C$_{26}$H$_{29}$NO.0.75H$_2$O: C, 89.10, H, 7.98, N, 3.63; Found: C, 81.53, 81.44, H, 7.73, 7.70, N, 3.56, 3.57.
(g) NMR (CDCl$_3$, 300 MHz): 7.4–7.2(m, 5H), 6.0–5.8(m, 1H), 5.2–5.1(m, 2H), 3.8–3.4(m, 3H), 2.6–1.2(m, 16H); MS: 285.
(h) NMR (CDCl$_3$, 300 MHz): 7.4–7.2(m, 5H), 7.0–6.9(m, 3H), 3.6–3.4(m, 4H), 2.6–1.4(m, 13H); Anal. Calcd for C$_{20}$H$_{25}$NOS: 73.35, H, 7.69, N, 4.28, S, 9.79; Found: C, 72.72, 73.03, H, 7.72, 7.67, N, 4.13, 4.17, S, 9.20, 9.19.
(i) NMR (CDCl$_3$, 300 MHz, MH$_z$): 7.4–7.2(m, 5H), 3.8–3.7(m, 1H), 3.6–3.4(m, 2H), 2.6–1.9(m, 28H); Anal. Calcd for C$_{22}$H$_{33}$NO: C, 80.68, H, 10.16, N, 4.28, Found: C, 80.17, 80.25, H, 10.06, 9.95, N, 4.19, 4.22.
(j) NMR (CDCl$_3$, 300 MHz): 7.4–7.2(m, 5H), 3.8–3.7(m, 2H), 3.5(s, 3H), 2.5–1.0(m, 23H); HRMS: Calcd: 259.1936; Found: 259.1942.
(k) NMR (CDCl$_3$, 300 MHz): 7.35–7.15(m, 6H), 6.35–6.3(m, 1H), 6.25–6.2(m, 1H), 3.5(s, 2H), 3.55–3.45(m, 1H), 2.6–2.2(m, 3H), 2.15–1.4(m, 10H); MS: 311.
(l) NMR (CDCl$_3$, 300 MHz): 7.5(d, 2H, J=8), 7.4–7.2(m, 8H), 3.5(dd, 2H, J=14, 9), 3.8–3.6(m, 2H), 3.5–2.4(m, 13H) ; MS: 321.
(m) NMR (CDCl$_3$, 300 MHz): 7.35–7.15(m, 10H), 3.5(dd, 2H, J=12, 10), 2.75(s, 2H), 2.65(br d, 1H, J=8), 2.45(dd, 14, J=8, 1), 1.7(m, 7H), 1.5–1.1(m, 6H); MS: 335.

EXAMPLE 43

Cis-2,6-Dibenzyl-6-hydroxy decahydroisoquinoline hydrochloride salt

Cis-2, 6-Dibenzyl-6-hydroxydecahydroisoquinoline (Example 42, 300 mg) was dissolved in ethanol (10 mL). A saturated solution of hydrogen chloride in ether (3 mL) was added with stirring. The mixture was concentrated in vacuo. The residue was triturated with copious amounts of diethyl ether and filtered. Drying in vacuo at 60° C. afforded a white solid (240 mg): mp 232° C.; Anal. Calcd for C$_{23}$H$_{29}$NO.HCl: C, 74.27, H, 8.13, N, 3.77, C$_{1, 9.53}$, Found: C, 74.10, H, 8.22, N, 3.38, Cl, 9.40.

EXAMPLES 44 to 48

Examples 44 to 48 were prepared according to the general procedure described for Example 43, using the appropriate inert solvent and acid.

TABLE 4

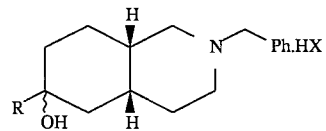

| Example | R | HX | mp (°C.) |
|---|---|---|---|
| 44 | 4-t-Bu | fumarate | 97–98 (a) |
| 45 | allyl | HCl | 138 (b) |
| 46 | 2-furyl | HCl | 137–138 (c) |
| 47 | phenyl | HCl | 135–136 (d) |
| 48 | benzyl | HCl | 232 (e) |

Footnotes to Table 4
(a) NMR (DMSO-$d_6$, 300 MHz): 7.5–7.3(m, 5H), 6.65(s, 2H), 4.0–3.25(m, 6H), 3.1–2.9(m, 1H), 2.8–2.75(m, 1H), 2.3–2.05(m, 1H), 1.85–1.3(m, 6H), 1.15–1.05(m, 1H), 0.9(s, 9H); Anal. Calcd for $C_{20}H_{31}NO\cdot C_4H_4O_4\cdot1.2H_2O$: C, 65.64, H, 8.58, N, 3.18; Found: C, 65.43, 65.39, H, 8.32, 8.26, N, 3.28, 3.29.
(b) Anal. Calcd for $C_{19}H_{27}NO\cdot HCl\cdot1.2H_2O$: C, 66.44, H, 8.62, N, 4.07, Cl, 10.32; Found: C, 66.12, 66.04, H, 8.65, 8.72, N, 3.78, 3.79.
(c) NMR (DMSO-$d_6$, 300 MHz): 10.6–10.4(m, 1H), 7.6–7.5(m, 3H), 7.5–7.4(m, 2H), 6.55–6.45(m, 1H), 6.45–6.3(m, 1H), 6.25–6.15(m, 0.8H), 6.0–5.95(m, 0.2H), 4.4–4.2(m, 2H), 3.8–3.6(m, 2H), 3.2–2.6(m, 4H), 2.6–1.6(m, 8H).
(d) Anal. Calcd for $C_{22}H_{27}NO\cdot HCl\cdot0.25H_2O$: C, 72.91, H, 7.92, N, 3.86, Cl, 9.78, Found: C, 72.87, 72.72, H, 7.97, 7.94, N, 3.75, 3.75, Cl, 9.73, 9.80.
(e) Anal. Calcd for $C_{23}H_{29}NO\cdot HCl$: C, 74.27, H, 8.13, N, 3.77, Cl, 9.53; Found: C, 74.10, H, 8.22, N, 3.38, Cl, 9.40.

EXAMPLE 49

Trans-2-Benzoyl-6-hydroxy-6-(4-t-butyldimethylsilyl-oxy-phenyl)-decahydroisoquinoline A mixture of 1-bromo-4-t-butyldimethylsilyloxy-benzene (1.7 g, 3.9 mmol), magnesium mesh (0.1 g, 3.9 mmol) and anhydrous THF were stirred at reflux temperature under a nitrogen atmosphere for 2 h. The reaction mixture was cooled to room temperature and transferred via syringe to a stirred semi-solution of trans-2-benzoyl-6-oxodecahydroisoquinoline (1.0 g, 3.9 mmol) in anhydrous THF at −78° C. The reaction mixture was warmed gradually to ambient temperature over 17.5 h. The reaction mixture was poured onto a saturated ammonium chloride solution, mixed, basified with a 1N NaOH solution and extracted three times with ethyl acetate. The combined organic layers were dried over magnesium sulfate, filtered and concentrated in vacuo. Column chromatography (ethyl acetate) gave the product, a solid (747 mg): mp 103°–104° C.; NMR (CDCl$_3$, 300 MHz): 7.5–7.3 (m, 7H), 6.85 (dd, 2H, J=8, 6), 4.9–4.6 (m, 1H), 3.9–3.55 (m, 1H), 3.1–2.4 (m, 2H), 1.9–1.0 (m, 9H), 0.95 (s, 9H), 0.25 (s, 3H), 0.2 (s, 3H); HRMS: Calcd: 465.2700, Found: 465.2689; Anal. Calcd for $C_{28}H39NO3Si$: C, 72.23, H, 8.44, N, 3.01; Found: C, 71.99, H, 8.61, N, 2.87.

EXAMPLE 50

Trans-2-Benzyl-6-hydroxy-6(4'-hydroxyphenyl)-decahydroisoquinoline

A mixture of trans-2-benzoyl-6-hydroxy-6-(4'-t-butyldimethylsilyloxyphenyl)decahydroisoquinoline (Example 48, 740 mg, 1.61 mmol) and lithium aluminum hydride (0.31 g, 8 mmol) in anhydrous THF (20 mL) was stirred at reflux temperature under a nitrogen atmosphere for 19.5 h. The reaction mixture was cooled to room temperature and quenched with excess ethyl acetate, followed by water (0.3 mL), a 1N NaOH solution (0.3 mL) and water (1 mL). The precipitate was filtered through celite; the filtrate was dried over magnesium sulfate and filtered. Removal of solvent in vacuo gave an oil. Column chromatography (ethyl acetate) gave the product, a solid (209 mg): mp 108°–109° C., NMR (CDCl$_3$, 200 MHz): 7.4–7.2 (m, 7H), 6.8 (d, 2H, J=7), 3.55 (s, 2H), 2.95 (br d, 1H, J=8), 2.85 (br d, 1H, J=8), 2.2 (s, 2H), 2.1–1.2 (m, 11H); Anal. Calcd for $C_{22}H_{27}NO_2\cdot0.3H_2O$: C, 77.06, H, 8.11, N, 4.09; Found C, 76.82, 76.83, H, 7.95, 8.15, N, 3.88, 3.80.

EXAMPLE 51

Trans-2-Benzoyl-6-hydroxy-6-(4'-methoxyphenyl)-decahydroisoquinoline

Following the procedure described in Example 48, 4-bromoanisole (0.73g, 0.49 mL, 3.9 mmol), magnesium mesh (0.1 g, 3.9 mmol) and trans-2-benzoyl-6-oxodecahydroisoquinoline (1.0 g, 3.9 mmol) were reacted in anhydrous THF to give the product, an oil (219 mg): NMR (CDCl$_3$, 270 MHz): 7.45–7.3 (m, 7H), 6.85 (d, 2H, J=8), 4.9–4.65 (m, 1H), 3.8 (s, 3H), 3.15–3.0 (m, 1H), 2.85–2.7 (m, 1H), 2.5–2.4 (m, 1H), 1.95–1.1 (m, 10H); HRMS: Calcd: 365.1991, Found: 365.1991.

EXAMPLE 52

Trans-2-Benzyl-6-hydroxy-6-(4'-methoxyphenyl)-decahydroisoquinoline

Following the general procedure described in Example 49, trans-2-benzoyl-6-hydroxy-6-(4'-methoxyphenyl-)decahydroisoquinoline (219 mg, 0.6 mmol) and lithium aluminum hydride (0.14 g, 3.6 mmol) were reacted in anhydrous THF (10 mL). Column chromatography (chloroform: methanol::9:1) afforded the product, a solid (158 mg): mp 38°–40° C.; NMR (CDCl$_3$, 200 MHz): 7.4 (d, 2H, J=8), 7.35–7.2 (m, 5H), 6.85 (d, 2H, J=8), 3.8 (s, 3H), 3.55 (s, 2H), 2.95 (br d, 1H, J=10), 2.85 (br d, 1H, J=10), 2.05 (br t, 1H, J=8), 1.85–1.7 (m, 4H), 1.6–1.3 (m, 7H); HRMS: Calcd: 351.2198, Found: 351.2193.

EXAMPLE 53

Trans-2-Benzoyl-6-(4'-fluorophenoxy)-decahydroisoquinoline

Part A: Methanesulfonyl chloride (1.14 g, 0.77 mL, 10 mmol) was added dropwise to a mixture of trans-2-benzoyl-6-hydroxydecahydroisoquinoline (Example 5), 1.36 g, 5 mmol), triethylamine (3.0 g, 4.2 mL, 30 mmol) and dichloromethane (20 mL) with stirring in an ice-water bath under a nitrogen atmosphere. The reaction mixture was stirred at 0°–5° C. for 30 min, transferred to a separatory funnel, and washed once with an ice-cold 1N HCl solution (20 mL), twice with a saturated sodium bicarbonate solution and once with brine. The organic solution was dried over magnesium sulfate and filtered. Removal of solvent in vacuo afforded the crude trans- 2-benzoyl-6-(methanesulfonyloxy)decahydroisoquinoline.

Part B: Sodium hydride (50% in oil, 0.48 g, 10 mmol) was washed twice with hexanes and decanted twice. N,N-Dimethylformamide (20 mL) was added. 4-Fluorophenol (1.12 g, 10 mmol) was added portionwise with stirring; gas evolution occurred. The reaction mixture was stirred under a nitrogen atmosphere for 30 min. A solution of the crude mesylate from Part A in N,N-dimethyl formamide (5 mL) was added dropwise. The reaction mixture was heated to 80°–90° C. and stirred for 19 h. The reaction mixture was cooled to ambient temperature and carefully quenched with water. Solvent was distilled in vacuo. The residue was taken up in a 1N NaOH solution and extracted three times with ethyl acetate. The combined organic layers were dried over magnesium sulfate, and concentrated in vacuo. Column chromatography (ethyl acetate:hexanes::1:1) gave the product, a solid (449 mg): NMR (CDCl$_3$, 300 MHz): 7.3–7.15 (m, 5H), 6.95 (t, 2H, J=8), 6.9–6.8 (m, 2H), 4.9–4.65 (m, 1H), 4.45 (br s, 1H), 3.9–3.55 (m, 1H), 3.15–2.95 (m, 1H), 2.9–2.65 (m, 1H), 2.55–2.4 (m, 1H), 2.25–2.0 (m, 2H), 1.8–1.1 (m, 7H); HRMS: Calcd: 353.1791, Found: 353.1798.

EXAMPLES 54 TO 95

Examples 54 to 95 may be prepared by the general procedure described in Example 53, using the appropriate hydroxybenzene derivative and solvent.

TABLE 5

| Example | R |
|---|---|
| 54 | 4-Cl |
| 55 | 4-Br |
| 56 | 4-I |
| 57 | 3-F |
| 58 | 3-Cl |
| 59 | 3-Br |
| 60 | 3-I |
| 61 | 2-F |
| 62 | 2-Cl |
| 63 | 4-Et |
| 64 | 3-Et |
| 65 | 4-CH$_3$ |
| 66 | 3-CH$_3$ |
| 67 | 4-OCH$_3$ |
| 68 | 3-OCH$_3$ |
| 69 | 3-N(CH$_3$)$_2$ |
| 70 | 4-NO$_2$ |
| 71 | 3-NO$_2$ |
| 72 | 4-t-C$_4$H$_9$ |
| 73 | 4-COCH$_3$ |
| 74 | 4-CN |
| 75 | 4-CON(CH$_3$)$_2$ |
| 76 | 4-C$_6$H$_5$ |
| 77 | 3-COCH$_3$ |
| 78 | 3-CN |
| 79 | 4-SCH$_3$ |
| 80 | 3-SCH$_3$ |
| 81 | 3,4-F$_2$ |
| 82 | 3,4-Cl$_2$ |
| 83 | 3,4-(CH$_3$O)$_2$ |
| 84 | 2,4-Cl$_2$ |
| 85 | 3,5-Cl$_2$ |
| 86 | 2,4-F$_2$ |
| 87 | 3,4-(CH$_3$)$_2$ |
| 88 | 3-(OC$_2$H$_5$)-4-OCH$_3$ |
| 89 | F$_5$ |
| 90 | Cl$_5$ |
| 91 | 2,3,5,6-F$_4$ |
| 92 | 2,3,5,6-Cl$_4$ |
| 93 | 4-C$_6$H$_5$O |
| 94 | 4-F-C$_6$H$_4$ |
| 95 | 4-CH$_3$O—C$_6$H$_4$ |

EXAMPLE 96

Cis-2-benzoyl-6-(4'-fluorophenoxy)decahydroisoquinoline

Following the general procedure described in Example 52, cis-2-benzoyl-6-hydroxy-decahydroisoquinoline (1.36 g, 5.3 mmol), methanesulfonyl chloride (1.14 g, 0.77 mL, 10 mmol), triethylamine (3.0 g, 4.2 mL, 30 mmol), dichloromethane (20 mL), sodium hydride (50% in oil, 0.48 g, 10 mmol), 4-fluorophenol (1.12 g, 10 mmol) and N,N-dimethylformamide (20 mL) were used to make the product (800 mg): 7.5–7.3 (m, 7H), 7.0 (t, 1H, J=8), 6.9–6.8 (m, 1H), 5.8–5.6 (m, 1H), 4.9–4.5 (m, 2H), 3.9–3.6 (m, 2H), 3.15–3.0 (m, 1H), 2.9–2.6 (m, 1H), 2.6–2.4 (m, 1H), 2.3–1.1 (m, 11H); HRMS: Calcd: 353.1791, Found: 353.1788.

EXAMPLES 97 TO 137

Examples 97 to 137 may be prepared according to the general procedure described in Example 52, using the appropriate hydroxybenzene derivative and solvent.

TABLE 6

| Example | R |
|---|---|
| 97 | H |
| 98 | 4-Cl |
| 99 | 4-Br |
| 100 | 4-I |
| 101 | 3-F |
| 102 | 3-Cl |
| 103 | 3-Br |
| 104 | 3-I |
| 105 | 2-F |
| 106 | 2-Cl |
| 107 | 4-CH$_3$ |
| 108 | 3-CH$_3$ |
| 109 | 4-OCH$_3$ |
| 110 | 3-OCH$_3$ |
| 111 | 3-N(CH$_3$)$_2$ |
| 112 | 4-NO$_2$ |
| 113 | 3-NO$_2$ |
| 114 | 4-t-C$_4$H$_9$ |
| 115 | 4-COCH$_3$ |
| 116 | 4-CN |
| 117 | 4-CON(CH$_3$)$_2$ |
| 118 | 4-C$_6$H$_5$ |
| 119 | 3-COCH$_3$ |
| 120 | 3-CN |
| 121 | 4-SCH$_3$ |
| 122 | 3-SCH$_3$ |
| 123 | 3,4-F$_2$ |
| 124 | 3,4,-Cl$_2$ |
| 125 | 3,4-(CH$_3$O)$_2$ |
| 126 | 2,4-Cl$_2$ |
| 127 | 3,5-Cl$_2$ |
| 128 | 2,4-F$_2$ |
| 129 | 3,4-(CH$_3$)$_2$ |
| 130 | 3-(OC$_2$H$_5$)-4-(OCH$_3$) |
| 131 | F$_5$ |
| 132 | Cl$_5$ |
| 133 | 2,3,5,6-F$_4$ |
| 134 | 2,3,5,6-Cl$_4$ |
| 135 | 4-C$_6$H$_5$O |
| 136 | 4-F-C$_6$H$_4$ |
| 137 | 4-CH$_3$OC$_6$H$_4$ |

EXAMPLES 138 TO 141

Examples 138 to 141 may be prepared by the general procedure described in Example 52, using the appropriate hydroxy compound and solvent.

TABLE 7

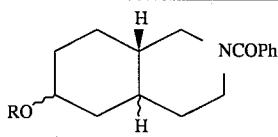

| Example | Ring Fusion | R |
|---|---|---|
| 138 | cis | 2-naphthyl |
| 139 | trans | 2-naphthyl |
| 140 | cis | 4-pyridyloxy |
| 141 | trans | 4-pyridyloxy |

EXAMPLE 142

Cis-2-Benzyl-6-(4'-fluorophenoxy)decahydroisoquinoline

A mixture of cis-2-benzoyl-6-(4'-fluoro-phenoxy)decahydroisoquinoline (Example 96) (832 mg, 2.36 mmol) and lithium aluminum hydride (0.38 g, 10 mmol) in anhydrous THF (10 mL) was stirred at reflux temperature under a nitrogen atmosphere for 14.5 h. The reaction mixture was cooled to room temperature and quenched with excess ethyl acetate, water (1 mL), a 1N NaOH solution (1 mL) and water (3 mL). The mixture was filtered through celite; the filtrate was dried over magnesium sulfate and filtered again. Removal of solvent in vacuo gave an oil.

Column chromatography (ethyl acetate) gave the product, a solid (166 mg) as a mixture of epimers: mp 94°–95° C.; NMR (CDCl$_3$, 300 MHz): 7.2–7.2 (m, 5H), 7.0–6.9 (m, 2H), 6.9–6.8 (m, 2H), 4.65–4.6 (m, 0.1H), 4.5 (t, 0.9 H, J=1), 3.5 (s, 2M), 2.9 (br d, 1H, J=10), 2.8 (br d, 1H, J=10), 2.1–1.95 (m, 3H), 1.75 (t, 1H, J=8), 1.6–1.2 (m, 8H); HRMS: Calcd: 339.1999, Found: 339.1998.

EXAMPLES 143 TO 228

Examples 143 to 228 may be prepared according to the general procedures described in Example 142, using the appropriate reducing agent, solvent and starting material from Examples 97 to 137.

TABLE 8

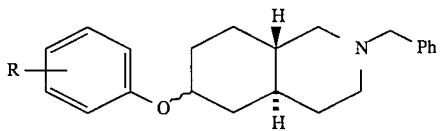

| Example | R |
|---|---|
| 143 | H |
| 144 | 4-Cl |
| 145 | 4-Br |
| 146 | 4-I |
| 147 | 3-F |
| 148 | 3-Cl |
| 149 | 3-I |
| 150 | 2-F |
| 151 | 2-Cl |
| 152 | 4-CH$_3$ |
| 153 | 3-CH$_3$ |
| 154 | 4-OCH$_3$ |
| 155 | 3-OCH$_3$ |
| 156 | 3-N(CH$_3$)$_2$ |
| 157 | 4-NH$_2$ |
| 158 | 3-NH$_2$ |
| 159 | 4-t-C$_4$H$_9$ |

TABLE 8-continued

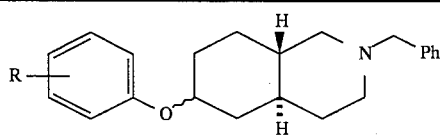

| Example | R |
|---|---|
| 160 | 4-CH(OH)CH$_3$ |
| 161 | 4-CH$_2$NH$_2$ |
| 162 | 4-CH$_2$N(CH$_3$)$_2$ |
| 163 | 4-C$_6$H$_5$ |
| 164 | 3-CH(OH)CH$_3$ |
| 165 | 3-CH$_2$NH$_2$ |
| 166 | 4-SCH$_3$ |
| 167 | 3-SCH$_3$ |
| 168 | 3,4-F$_2$ |
| 169 | 3,4-Cl$_2$ |
| 170 | 3,4-(CH$_3$O)$_2$ |
| 171 | 2,4-Cl$_2$ |
| 172 | 3,5-Cl$_2$ |
| 173 | 2,4-F$_2$ |
| 174 | 3,4-(CH$_3$)$_2$ |
| 175 | 3-(OC$_2$H$_5$)-4-(OCH$_3$) |
| 176 | F$_5$ |
| 177 | Cl$_5$ |
| 178 | 2,3,5,6-F$_4$ |
| 179 | 2,3,5,6-Cl$_4$ |
| 180 | 4-C$_6$H$_5$O |
| 181 | 4-F-C$_6$H$_4$ |
| 182 | 4-CH$_3$O—C$_6$H$_4$ |

TABLE 9

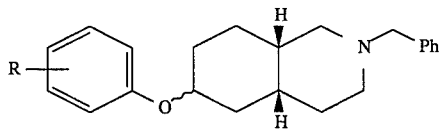

| Example | R | mp (°C.) |
|---|---|---|
| 183 | H | |
| 184 | 4-F | 94 (a) |
| 185 | 4-Cl | |
| 186 | 4-Br | |
| 187 | 4-I | |
| 188 | 3-F | |
| 189 | 3-Cl | |
| 190 | 3-Br | |
| 191 | 3-I | |
| 192 | 2-F | |
| 193 | 2-Cl | |
| 194 | 4-CH$_3$ | |
| 195 | 3-CH$_3$ | |
| 196 | 4-OCH$_3$ | |
| 197 | 3-OCH$_3$ | |
| 198 | 3-N(CH$_3$)$_2$ | |
| 199 | 4-NH$_2$ | |
| 200 | 3-NH$_2$ | |
| 201 | 4-t-C$_4$H$_9$ | |
| 202 | 4-CH(OH)CH$_3$ | |
| 203 | 4-CH$_2$NH$_2$ | |
| 204 | 4-CH$_2$N(CH$_3$)$_2$ | |
| 205 | 4-C$_6$H$_5$ | |
| 206 | 3-CH(OH)CH$_3$ | |
| 207 | 3-CH$_2$NH$_2$ | |
| 208 | 4-SCH$_3$ | |
| 209 | 3-SCH$_3$ | |
| 210 | 3,4-F$_2$ | |
| 211 | 3,4-Cl$_2$ | |
| 212 | 3,4-(CH$_3$O)$_2$ | |
| 213 | 2,4-Cl$_2$ | |
| 214 | 3,5-Cl$_2$ | |
| 215 | 2,4-F$_2$ | |

TABLE 9-continued

R—[phenyl]—O—[decahydroisoquinoline with H stereochemistry]—CH₂—N—CH₂—Ph

| Example | R | mp (°C.) |
|---|---|---|
| 216 | 3,4-(CH$_3$)$_2$ | |
| 217 | 3-(OC$_2$H$_5$)-4-(OCH$_3$) | |
| 218 | F$_5$ | |
| 219 | Cl$_5$ | |
| 220 | 2,3,5,6-F$_4$ | |
| 221 | 2,3,5,6-Cl$_4$ | |
| 222 | 4-C$_6$H$_5$O | |
| 223 | 4-F-C$_6$H$_4$ | |
| 224 | 4-CH$_3$OC$_6$H$_4$ | |

Footnotes for Table 9
(a) Anal. Calcd for C$_{22}$H$_{26}$FNO: C, 77.84, H, 7.72, N, 4.13, F, 5.60; Found: C, 77.53, H, 7.72, N, 4.05, F, 5.33.

TABLE 10

RO—[decahydroisoquinoline]—CH₂—N—CH₂—Ph

| Example | Ring Fusion | R |
|---|---|---|
| 225 | cis | 2-naphthyl |
| 226 | trans | 2-naphthyl |
| 227 | cis | 4-pyridyl |
| 228 | trans | 4-pyridyl |

EXAMPLE 229

Cis-2-Benzyl-6-(4'-fluorobenzyloxy)-decahydroisoquinoline

A mixture of cis-2-benzyl-6-hydroxydecahydroisoquinoline (Example 2, 0.87 g, 5.3 mmol) and sodium hydride (50% in oil, 0.48 g, 10 mmol, prewashed with hexanes) in anhydrous THF (50 mL) was stirred for 30 min. 4-Fluorobenzyl bromide (1.89 g, 10 mmol) was added and the reaction mixture was stirred at reflux temperature under a nitrogen atmosphere for 16 h. The reaction mixture was cooled to ambient temperature, quenched with methanol, poured onto water and extracted three times with ethyl acetate. The combined organic layers were dried over magnesium sulfate, filtered and concentrated in vacuo. Column chromatography (chloroform:methanol::9:1, then ethyl acetate: hexanes:: 1:1) afforded the product, an oil (200 mg): NMR (CDCl$_3$, 300 MHz): 7.3–7.2 (m, 7H), 7.05 (t, 2H, J=7), 4.5 (s, 2H), 3.55–3.3 (m, 2H), 2.7–1.0 (m, 25H), 1.0–0.8 (m, 5H); MS:353.

EXAMPLES 230 TO 272

Examples 230 to 272 may be prepared according to the general procedure described in Example 229, using the appropriate alcohol, halide, base and solvent.

TABLE 11

R—[phenyl]—CH$_2$O—[decahydroisoquinoline]—CH₂—N—CH₂—Ph

| Example | R | mp (°C.) |
|---|---|---|
| 230 | H | |
| 231 | 3-F | |
| 232 | 2-F | |
| 233 | 4-Cl | |
| 234 | 3-Cl | |
| 235 | 2-Cl | |
| 236 | 4-Br | |
| 237 | 4-CH$_3$ | |
| 238 | 4-OCH$_3$ | |
| 239 | 4-OTBDMS | (a) |
| 240 | 4-CH$_2$OTBDMS | |
| 241 | 4-SCH$_3$ | |
| 242 | 4-NO$_2$ | |
| 243 | 3,4-F$_2$ | |
| 244 | 3,4-Cl$_2$ | |
| 245 | 3,5-(CH$_3$O)$_2$ | |
| 246 | CO$_2$C$_2$H$_5$ | |
| 247 | H | |
| 248 | 4-F | |
| 249 | 3-F | |
| 250 | 2-F | |
| 251 | 4-Cl | |
| 252 | 3-Cl | |
| 253 | 2-Cl | |
| 254 | 4-Br | |
| 255 | 4-CH$_3$ | |
| 256 | 4-OCH$_3$ | |
| 257 | 4-OTBDMS | |
| 258 | 4-CH$_2$OTBDMS | |
| 259 | 4-SCH$_3$ | |
| 260 | 4-NO$_2$ | |
| 261 | 3,4-F$_2$ | |
| 262 | 3,4-Cl$_2$ | |
| 263 | 3,5-(OCH$_3$)$_2$ | |
| 264 | CO$_2$C$_2$H$_5$ | |

TABLE 12

RO—[decahydroisoquinoline]—CH₂—N—CH₂—Ph

| Example | Ring Fusion | R |
|---|---|---|
| 265 | cis | CH$_3$ |
| 266 | trans | CH$_3$ |
| 267 | cis | allyl |
| 268 | trans | allyl |
| 269 | cis | 2-naphthylmethyl |
| 270 | trans | 2-naphthylmethyl |
| 271 | cis | 4-pyridylmethyl |
| 272 | trans | 4-pyridylmethyl |

EXAMPLE 273

Cis-2-Benzyl-6-(4'-fluorobenzyloxy)-decahydro-
isoquinoline, hydrochloride salt

Cis-2-Benzyl-6-(4'-fluorobenzyloxy)-deca-hydroisoquinoline (200 mg) was dissolved in ether with stirring. A saturated solution of hydrogen chloride in ether was added with stirring. The precipitate was filtered and triturated with copious amounts of ether. Drying in vacuo at 60° C. afforded a solid (100 mg): mp 240° C.; Anal. Calcd for $C_{23}H_{28}FNO \cdot HCl \cdot 0.5H_2O$: C, 69.25, H, 7.32, N, 3.51, F, 4.76; Found: C, 69.39, 69.37, H, 7.43, 7.37, N, 3.38, 3.50, F, 4.88, 4.69.

TABLE 13

| Example | Ring Fusion | R |
|---|---|---|
| 273 | Cis | (4-F-C6H4)-CH2- |
| 274 | Trans | (CH2)3CO-(4-F-C6H4)- |
| 275 | Cis | piperidinyl-C(=O)-C(=CH-)-CH2CH2CH3 with pyridine |
| 276 | Trans | thiazole-containing acyl group |

Utilities Section

The compounds of this invention and their pharmaceutically acceptable salts possess psychotropic properties, particularly antipsychotic activity of good duration with selective sigma receptor antagonist activities while lacking the typical movement disorder side-effects of standard dopamine receptor antagonist antipsychotic agents. These compounds may also be useful as antidotes for certain psychotomimetic agents such as phencyclidine (PCP), and as antidyskinetic agents.

In Vitro

Sigma Receptor Binding Assay

Male Hartley guinea pigs (250–300 g, Charles River) were sacrificed by decapitation. Brain membranes were prepared by the method of Tam (Proc. Natl. Acad. Sci. USA 80: 6703–6707, 1983). Whole brains were homogenized (20 seconds) in 10 vol (wt/vol) of ice-cold 0.34 M sucrose with a Brinkmann Polytron (setting 8). The homogenate was centrifuged at 920×g for 10 minutes. The supernatant was centrifuged at 47,000×g for 20 minutes. The resulting membrane pellet was resuspended in 10 vol (original wt/vol) of 50 mM Tris HCl (pH 7.4) and incubated at 37° C. for 45 minutes to degrade and dissociate bound endogenous ligands. The membranes were then centrifuged at 47,000×g for 20 minutes and resuspended in 50 mM Tris HCl (50 mL per brain).

0.5 mL aliquots of the membrane preparation were incubated with unlabeled drugs, 1 nM $(+)$-$[^3H]$SKF 10,047 in 50 mM Tris HCl, pH 7.4, in a final volume of 1 mL. Nonspecific binding was measured in the presence of 10 μM (+)-SKF 10,047. The apparent dissociation constant (Kd) for $(+)$-$[^3H]$SKF 10,047 is 50 nM. After 45 minutes of incubation at room temperature, samples were filtered rapidly through Whatman GF/C glass filters under negative pressure, and washed 3 times with ice-cold Tris buffer (5 mL).

$IC_{50}$s were calculated from log-logit plots. Apparent $K_i$s were calculated from the equation, $K_i=IC_{50}/[1+(L/K_d)]$ (4), where L is the concentration of radioligand and $K_d$ is its dissociation constant. Data are shown in Table A.

Dopamine Receptor Binding

Membranes were prepared from guinea pig striatum by the method described for sigma receptor binding. The membranes were then resuspended in 50 mM Tris HCl (9 mL per brain).

0.5 mL aliquots of the membrane preparation were incubated with unlabeled drugs, and 0.15 nM $[^3H]$spiperone in a final volume of 1 mL containing 50 mM Tris HCl, 120 mM NaCl and 1 mM $MgCl_2$(pH 7.7). Nonspecific binding was measured in the presence of 100 nM (+)-butaclamol. After 15 minutes of incubation at 37° C., samples were filtered rapidly through Whatman GF/C glass filters under negative pressure, and washed three times with ice-cold binding buffer (5 mL).

$IC_{50}$s were calculated from log-logit plots. Apparent $K_i$s were calculated from the equation $K_i=IC_{50}[1+(L/K_d)]$(4), where L is the concentration of radioligand and $K_d$ is its dissociation constant. Data are shown in Table A.

The examples of this invention shown in Table A indicate potent binding affinity for sigma receptors. Therefore these compounds are not expected to produce the extrapyramidal symptoms that are typical of that produced by haloperidol and other typical antipsychotics that are dopamine receptor antagonists.

TABLE A

| | Receptor Binding Affinities | |
|---|---|---|
| Example | Sigma | Dopamine D-2 |
| Haloperidol | +++ | +++ |
| 2 | ++ | − |
| 3 | ++ | − |
| 4 | ++ | − |
| 7 | +++ | − |
| 9 | +++ | − |
| 10 | +++ | − |
| 11 | ++ | − |
| 12 | +++ | − |
| 13 | ++ | − |
| 14 | + | − |
| 15 | +++ | − |
| 16 | +++ | − |

TABLE A-continued

| | Receptor Binding Affinities | |
|---|---|---|
| Example | Sigma | Dopamine D-2 |
| 18 | +++ | − |
| 20 | ++ | − |
| 21 | + | − |
| 22 | +++ | − |
| 24 | +++ | ++ |
| 27 | +++ | − |
| 30 | ++ | − |
| 31 | +++ | − |
| 32 | ++ | − |
| 33 | +++ | − |
| 35 | +++ | − |
| 37 | +++ | − |
| 38 | +++ | − |
| 39 | + | − |
| 43 | +++ | − |
| 44 | +++ | − |
| 45 | ++ | − |
| 46 | +++ | − |
| 47 | +++ | − |
| 48 | +++ | − |
| 49 | + | − |

In Vivo

Isolation-Induced Aggression in Mice

This is a modification of the method of Yen et al. (Arch. Int. Pharmacodyn. 123: 179–185, 1959) and Jannsen et al. (J. Pharmacol. Exp. Ther. 129: 471–475, 1960). Male Balb/c mice (Charles River) were used. After 2 weeks of isolation in plastic cages (11.5×5.75×6 in) the mice were selected for aggression by placing a normal group-housed mouse in the cage with the isolate for a maximum of 3 minutes. Isolated mice failing to consistently attack an intruder were eliminated from the colony.

Drug testing was carried out by treating the isolated mice with test drugs or standards. Fifteen minutes after dosing with test drugs by the oral route, one isolated mouse was removed from its home cage and placed in the home cage of another isolate. Scoring was a yes or no response for each pair. A maximum of 3 minutes was allowed for an attack and the pair was separated immediately upon an attack. Selection of home cage and intruder mice was randomized for each test. Mice were treated and tested twice a week with at least a 2 day washout period between treatments. Treatments are shown in Table B.

TABLE B

| Example | Oral Anti-Isolation-induced Aggression Activity in Mice |
|---|---|
| Haloperidol | +++ |
| 10 | ++ |
| 15 | +++ |
| 17 | ++ |

Induction of Catalepsy

This is a modification of the method of Costall and Naylor (Psychopharmacologia (Berl.), 43, 69–74, 1975). Male CD rats (Charles River) weighing 250–300 g were treated with test drugs and standards by the oral route and tested for the presence of catalepsy 30 minute, 60 minute, and 90 minute after treatment. To test for catalepsy, each rat is placed with its front paws over a 10 cm high horizontal bar. The intensity of catalepsy is measured by the length of time it takes the animal to move both forelegs to the table. A time of 20 seconds is considered maximal catalepsy. Results are shown in Table C.

TABLE C

| Example | Oral Catalepsy Activity in Rats |
|---|---|
| Haloperidol | ++++ |
| 15 | − |
| 27 | − |

Dosage Forms

Daily dosage ranges from 1 mg to 2000 mg. Dosage forms (compositions) suitable for administration ordinarily will contain 0.5–95% by weight of the active ingredient based on the total weight of the composition.

The active ingredient can be administered orally in solid dosage forms, such as capsules, tablets, and powders, or in liquid dosage forms, such as elixirs, syrups, and suspensions; it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, A. Osol, a standard reference text in this field.

What is claimed is:

1. A compound having the formula:

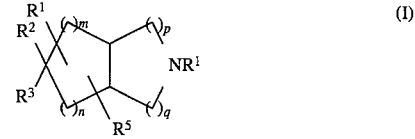

(I)

or a pharmaceutically acceptable salt or pro-drug thereof, wherein:

m is 1 or 2;

n is 1 or 2;

p is 1 or 2;

q is 1 or 2;

provided that m and n cannot both be 2 or p and q cannot both be 2;

$R^1$ may be H; alkyl of 1 to 6 carbons; cycloalkyl of 3 to 6 carbons; cycloalkyl-alkyl of 4 to 8 carbons; alkenyl of 3 to 6 carbons; phenyl-alkyl (1 to 6 carbons) where the phenyl group is optionally substituted by $R^6$ and $R^7$ and where the alkyl group is optionally substituted by oxo, hydroxyl groups or hydrogen; pyridyl; pyrimidinyl; pyrazinyl; quinolinyl; isoquinolinyl; indolyl; quinazolinyl; phthalizinyl; furanyl; thienyl; napthyridinyl; or naphthyl-alkyl (1 to 6 carbons) and where the alkyl group is optionally substituted by oxo, hydroxyl groups or hydrogen;

$R^1$ may also be drawn from the following groups:

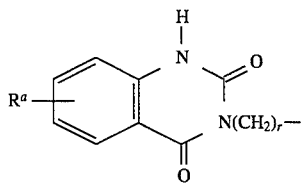

where:
r=1 or 2,
$R^a$=H, alkyl of 1 to 6 carbons, halogen, alkoxy of 1 to 6 carbons or OH, and

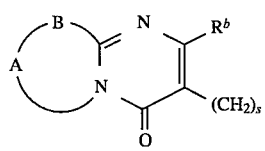

where:
S=1 or 2,
B=S, $CH_2$ or CH=CH,
A=$(CH_2)_2$, $(CH_2)_3$ or CH=CH,
$R^b$=H or alkyl of 1 to 6 carbons;

$R^2$ may be H, or OH, provided that when $R^2$ is OH then $R^3=R^{3a}$ and provided that when $R^2$ is H then $R^3=OR^{3a}$ or $SR^{3a}$;

$R^{2a}$ may be alkyl of 1 to 10 carbons or phenyl;

$R^{3a}$ may be alkyl of 1 to 6 carbons; phenyl optionally substituted by $R^6$ and $R^7$; phenyl-alkyl (1 to 6 carbons) where the phenyl group is optionally substituted by $R^6$ and $R^7$; cycloalkyl of 3 to 6 carbons; cycloalkyl-alkyl of 4 to 12 carbons; naphthyl; pyridyl; pyrimidinyl; pyrazinyl; quinolinyl; isoquinolinyl; indolyl; quinazolinyl; phthalizinyl; furanyl; thienyl; or napthyridinyl;

$R^4$ and $R^5$ may independently be H or alkyl of 1 to 6 carbons;

$R^6$ and $R^7$ independently are selected at each occurrence from the group consisting of H, alkyl of 1 to 6 carbons, alkenyl of 2 to 6 carbons, OH, alkoxy of 1 to 6 carbons, alkythio of 1 to 6 carbons, alkylsulfinyl of 1 of 6 carbons, alkylsulfonyl of 1 to 6 carbons, $NH_2$, alkylamino of 1 to 6 carbons, dialkylamino of 2 to 12 carbons, $NO_2$, alkanoylamino of 2 to 6 carbons, CN, $CO_2H$, carboalkoxy of 2 to 10 carbons, $CONH_2$ or $CONR^8R^9$; and $R^8$ and $R^9$ independently are H or alkyl of 1 to 6 carbons; or $R^8$ and $R^9$ taken together may be alkylene of 3 to 6 carbons.

2. A compound of claim 1 wherein $R^1$ is phenyl-alkyl (1 to 6 carbons) where the phenyl group is optionally substituted with $R^6$ or $R^7$ and where the alkyl group is optionally substituted with H; pyridyl; pyrimidinyl; pyrazinyl; quinolinyl; isoquinolinyl; indolyl; quinazolinyl; phthalizinyl; furanyl; thienyl; napthyridinyl; or naphthyl-alkyl (1 to 6 carbons).

3. A compound of claim 1 wherein $R^4$ is H.
4. A compound of claim 1 wherein $R^5$ is H.
5. A compound of claim 1 wherein m=2.
6. A compound of claim 1 wherein n=2.
7. A compound of claim 1 wherein p=2.
8. A compound of claim 1 wherein q=2.
9. A compound of claim 1 wherein:

$R^1$ is phenyl-alkyl (1 to 6 carbons) where the phenyl group is optionally substituted with $R^6$ or $R^7$ and where the alkyl group is optionally substituted with H; pyridyl; pyrimidinyl; pyrazinyl; quinolinyl; isoquinolinyl; indolyl; quinazolinyl; phthalizinyl; furanyl; thienyl; napthyridinyl; or naphthyl-alkyl (1 to 6 carbons);

$R^2$ is equal to H when $R^3$ is $OR^{3a}$ and $R^2$ is equal to OH when $R^3$ is $R^{3a}$;

$R^4$ is H;

$R^5$ is H;

$R^6$ and $R^7$ independently are H, alkyl of 1 to 6 carbons, alkenyl of 2 to 6 carbons, OH, alkoxy of 1 to 6 carbons, alkythio of 1 to 6 carbons, alkylsulfinyl of 1 of 6 carbons, alkylsulfonyl of 1 to 6 carbons, $NH_2$, alkylamino of 1 to 6 carbons, dialkylamino of 2 to 12 carbons, $NO_2$, alkanoylamino of 2 to 6 carbons, CN, $CO_2H$, carboalkoxy of 2 to 10 carbons, $CONH_2$ or $CONR^{11}R^{12}$;

provided that one of m or n is 2 and that m and q are equal and that n and p are equal.

10. The compound of claim 1 which is Cis-2-(4'-fluorophenethyl)- 6-(4"-fluorophenyl)-6-hydroxydecahydroisoquinoline.

11. The compound of claim 1 which is Cis-2-(4'-pyridylmethyl)- 6-(4"-fluorophenyl)-6-hydroxy decahydroisoquinoline.

12. The compound of claim 1 which is Cis-2-(4'-pyridylmethyl)- 6-(4"-fluorophenyl)-6 hydroxydecahydroisoquinoline.

13. The compound of claim 1 which is Trans-2-Benzyl-6-(4'-fluorophenyl)-6-hydroxy decahydroisoquinoline.

14. The compound of claim 1 which is Trans-2-Benzyl-6-(4'-fluorophenyl)-6-hydroxy decahydroisoquinoline.

15. The compound of claim 1 which is Trans-2-Benzyl-4-(4'-Fluorobenzyloxy)-decahydroisoquinoline.

16. The compound of claim 1 which is Trans-2-Benzyl-4-(4'-fluorophenoxy)-decahydroisoquinoline.

17. A pharmaceutical composition comprising a pharmaceutically acceptable carrier and an antipsychotic effective amount of a compound of claim 1.

18. A pharmaceutical composition comprising a pharmaceutically acceptable carrier and an antipsychotic effective amount of a compound of claim 2.

19. A pharmaceutical composition comprising a pharmaceutically acceptable carrier and an antipsychotic effective amount of a compound of claim 3.

20. A pharmaceutical composition comprising a pharmaceutically acceptable carrier and an antipsychotic effective amount of a compound of claim 4.

21. A pharmaceutical composition comprising a pharmaceutically acceptable carrier and an antipsychotic effective amount of a compound of claim 5.

22. A pharmaceutical composition comprising a pharmaceutically acceptable carrier and an antipsychotic effective amount of a compound of claim 6.

23. A pharmaceutical composition comprising a pharmaceutically acceptable carrier and an antipsychotic effective amount of a compound of claim 7.

24. A pharmaceutical composition comprising a pharmaceutically acceptable carrier and an antipsychotic effective amount of a compound of claim 8.

25. A pharmaceutical composition comprising a pharmaceutically acceptable carrier and an antipsychotic effective amount of a compound of claim 9.

26. A pharmaceutical composition comprising a pharmaceutically acceptable carrier and an antipsychotic effective amount of a compound of claim 10.

27. A pharmaceutical composition comprising a pharmaceutically acceptable carrier and an antipsychotic effective amount of a compound of claim 11.

28. A pharmaceutical composition comprising a pharmaceutically acceptable carrier and an antipsychotic effective amount of a compound of claim 12.

29. A pharmaceutical composition comprising a pharmaceutically acceptable carrier and an antipsychotic effective amount of a compound of claim 13.

30. A pharmaceutical composition comprising a pharmaceutically acceptable carrier and an antipsychotic effective amount of a compound of claim 14.

31. A pharmaceutical composition comprising a pharmaceutically acceptable carrier and an antipsychotic effective amount of a compound of claim 15.

32. A pharmaceutical composition comprising a pharmaceutically acceptable carrier and an antipsychotic effective amount of a compound of claim 16.

33. A method for treatment of physiological or drug induced psychosis or dyskinesia in a mammal comprising administering to a mammal in need of such treatment an antipsychotic or antidyskinetic effective amount of a compound of claim 1.

34. A method for treatment of physiological or drug induced psychosis or dyskinesia in a mammal comprising administering to a mammal in need of such treatment an antipsychotic or antidyskinetic effective amount of a compound of claim 2.

35. A method for treatment of physiological or drug induced psychosis or dyskinesia in a mammal comprising administering to a mammal in need of such treatment an antipsychotic or antidyskinetic effective amount of a compound of claim 3.

36. A method for treatment of physiological or drug induced psychosis or dyskinesia in a mammal comprising administering to a mammal in need of such treatment an antipsychotic or antidyskinetic effective amount of a compound of claim 4.

37. A method for treatment of physiological or drug induced psychosis or dyskinesia in a mammal comprising administering to a mammal in need of such treatment an antipsychotic or antidyskinetic effective amount of a compound of claim 5.

38. A method for treatment of physiological or drug induced psychosis or dyskinesia in a mammal comprising administering to a mammal in need of such treatment an antipsychotic or antidyskinetic effective amount of a compound of claim 6.

39. A method for treatment of physiological or drug induced psychosis or dyskinesia in a mammal comprising administering to a mammal in need of such treatment an antipsychotic or antidyskinetic effective amount of a compound of claim 7.

40. A method for treatment of physiological or drug induced psychosis or dyskinesia in a mammal comprising administering to a mammal in need of such treatment an antipsychotic or antidyskinetic effective amount of a compound of claim 8.

41. A method for treatment of physiological or drug induced psychosis or dyskinesia in a mammal comprising administering to a mammal in need of such treatment an antipsychotic or antidyskinetic effective amount of a compound of claim 9.

42. A method for treatment of physiological or drug induced psychosis or dyskinesia in a mammal comprising administering to a mammal in need of such treatment an antipsychotic or antidyskinetic effective amount of a compound of claim 10.

43. A method for treatment of physiological or drug induced psychosis or dyskinesia in a mammal comprising administering to a mammal in need of such treatment an antipsychotic or antidyskinetic effective amount of a compound of claim 11.

44. A method for treatment of physiological or drug induced psychosis or dyskinesia in a mammal comprising administering to a mammal in need of such treatment an antipsychotic or antidyskinetic effective amount of a compound of claim 12.

45. A method for treatment of physiological or drug induced psychosis or dyskinesia in a mammal comprising administering to a mammal in need of such treatment an antipsychotic or antidyskinetic effective amount of a compound of claim 13.

46. A method for treatment of physiological or drug induced psychosis or dyskinesia in a mammal comprising administering to a mammal in need of such treatment an antipsychotic or antidyskinetic effective amount of a compound of claim 14.

47. A method for treatment of physiological or drug induced psychosis or dyskinesia in a mammal comprising administering to a mammal in need of such treatment an antipsychotic or antidyskinetic effective amount of a compound of claim 15.

48. A method for treatment of physiological or drug induced psychosis or dyskinesia in a mammal comprising administering to a mammal in need of such treatment an antipsychotic or antidyskinetic effective amount of a compound of claim 16.

* * * * *